(12) United States Patent
Soutorine et al.

(10) Patent No.: US 8,220,689 B2
(45) Date of Patent: Jul. 17, 2012

(54) DEVICE AND METHOD FOR DELIVERING SHAPE-MEMORY STAPLES

(75) Inventors: Mikhail Soutorine, Oakleigh (AU); Artem N Chernov-Haraev, Moscow (RU)

(73) Assignee: Endogene Pty Ltd, Victoria (AU)

( * ) Notice: Subject to any disclaimer, the term of this patent is extended or adjusted under 35 U.S.C. 154(b) by 436 days.

(21) Appl. No.: 12/603,987

(22) Filed: Oct. 22, 2009

(65) Prior Publication Data

US 2010/0102105 A1    Apr. 29, 2010

Related U.S. Application Data

(63) Continuation-in-part of application No. PCT/AU2008/000623, filed on May 2, 2008.

(60) Provisional application No. 61/162,462, filed on Mar. 23, 2009.

(30) Foreign Application Priority Data

May 2, 2007   (AU) ................................ 2007902314

(51) Int. Cl.
   *A61B 17/068*    (2006.01)
(52) U.S. Cl. ........ 227/176.1; 227/19; 606/139; 606/153
(58) Field of Classification Search ............... 227/19, 227/176.1, 175.1, 175.2; 606/139, 219, 151, 606/153, 142, 277
   See application file for complete search history.

(56) References Cited

U.S. PATENT DOCUMENTS

| | | | |
|---|---|---|---|
| 4,485,816 A | 12/1984 | Krumme | |
| 4,550,870 A | 11/1985 | Krumme et al. | |
| 5,586,983 A | 12/1996 | Sanders et al. | |
| 5,707,380 A * | 1/1998 | Hinchliffe et al. | 606/153 |
| 5,782,844 A * | 7/1998 | Yoon et al. | 606/139 |
| 6,024,748 A * | 2/2000 | Manzo et al. | 606/153 |
| 6,203,553 B1 * | 3/2001 | Robertson et al. | 606/139 |
| 6,709,442 B2 * | 3/2004 | Miller et al. | 606/153 |
| 7,004,958 B2 | 2/2006 | Adams et al. | |
| 7,335,212 B2 * | 2/2008 | Edoga et al. | 606/139 |
| 8,105,345 B2 * | 1/2012 | Golden et al. | 606/153 |
| 2002/0029044 A1 | 3/2002 | Monassevitch et al. | |

(Continued)

FOREIGN PATENT DOCUMENTS

EP    0 326 757 A1    8/1989

(Continued)

OTHER PUBLICATIONS

International Search Report of PCT/AU2008/000623, dated Jul. 1, 2008.

*Primary Examiner* — Scott A. Smith
(74) *Attorney, Agent, or Firm* — Hamre, Schumann, Mueller & Larson, P.C.

(57) ABSTRACT

An apparatus comprising a plurality of chambers for receiving an associated plurality of staples, each formed with a shape memory that allows the staple to adopt a straightened configuration, when placed in a stapler, and a deployed configuration for suturing when released from the stapler; and a sleeve moveable relative to the chambers between a first position, in which the staples are trapped by the sleeve within the chambers in the straightened configuration, and a second position, whereby the staples are freed to adopt the deployed configuration, wherein the sleeve is adapted to move between the first and second positions by rotating relative to the chambers.

10 Claims, 21 Drawing Sheets

U.S. PATENT DOCUMENTS

| | | |
|---|---|---|
| 2003/0045893 A1 | 3/2003 | Ginn |
| 2003/0139746 A1 | 7/2003 | Groiso |
| 2005/0070924 A1 | 3/2005 | Schaller et al. |
| 2005/0143763 A1 | 6/2005 | Ortiz et al. |
| 2006/0235446 A1 | 10/2006 | Godin |
| 2006/0282118 A1 | 12/2006 | Surti |

FOREIGN PATENT DOCUMENTS

| | | |
|---|---|---|
| EP | 1 683 490 | 7/2006 |
| EP | 2 039 316 | 3/2009 |
| FR | 2 694 696 | 2/1994 |
| FR | 2 747 911 | 10/1997 |
| RU | 2 046 602 | 10/1995 |
| WO | 96/16603 | 6/1996 |
| WO | 96/18352 | 6/1996 |
| WO | 98/58591 | 12/1998 |
| WO | 00/35355 | 6/2000 |
| WO | 00/64365 | 11/2000 |
| WO | 01/30230 | 5/2001 |
| WO | 02/19888 | 3/2002 |
| WO | 03/077730 | 9/2003 |
| WO | 2005/037055 | 4/2005 |
| WO | 2005/092212 | 10/2005 |
| WO | 2006/072934 | 7/2006 |
| WO | 2006/135642 | 12/2006 |
| WO | 2008/134812 | 11/2008 |
| WO | 2010/108213 | 9/2010 |

* cited by examiner

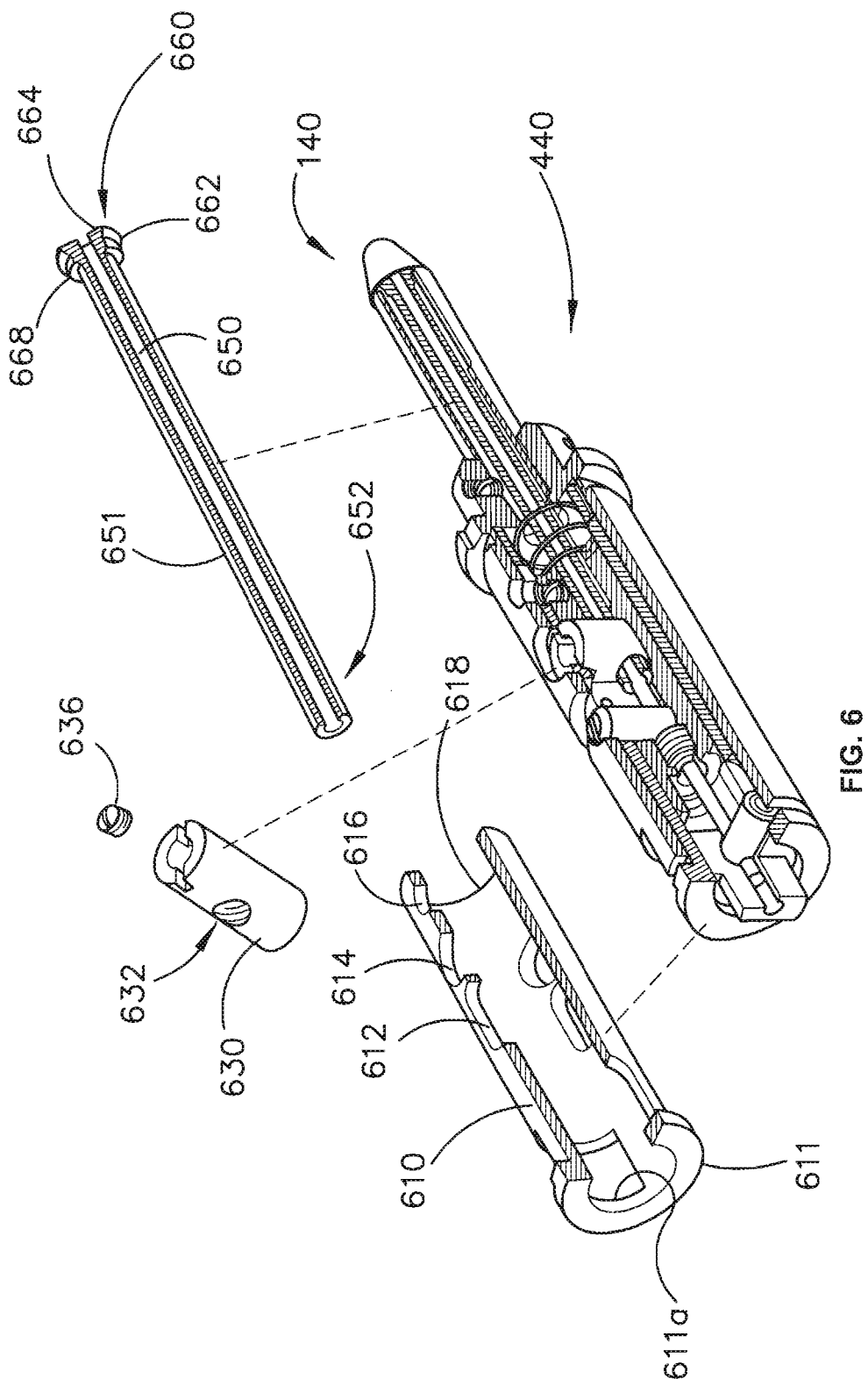

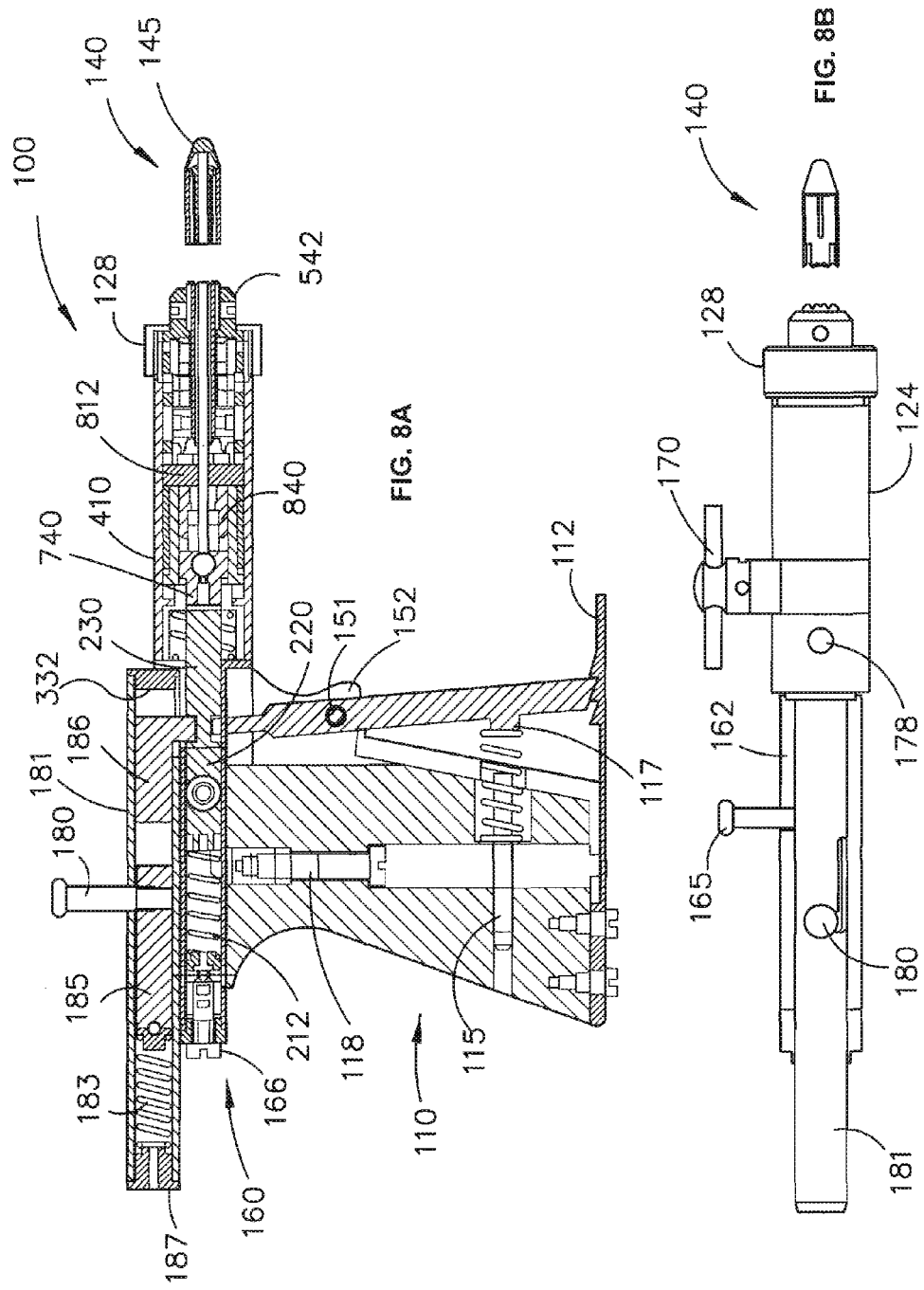

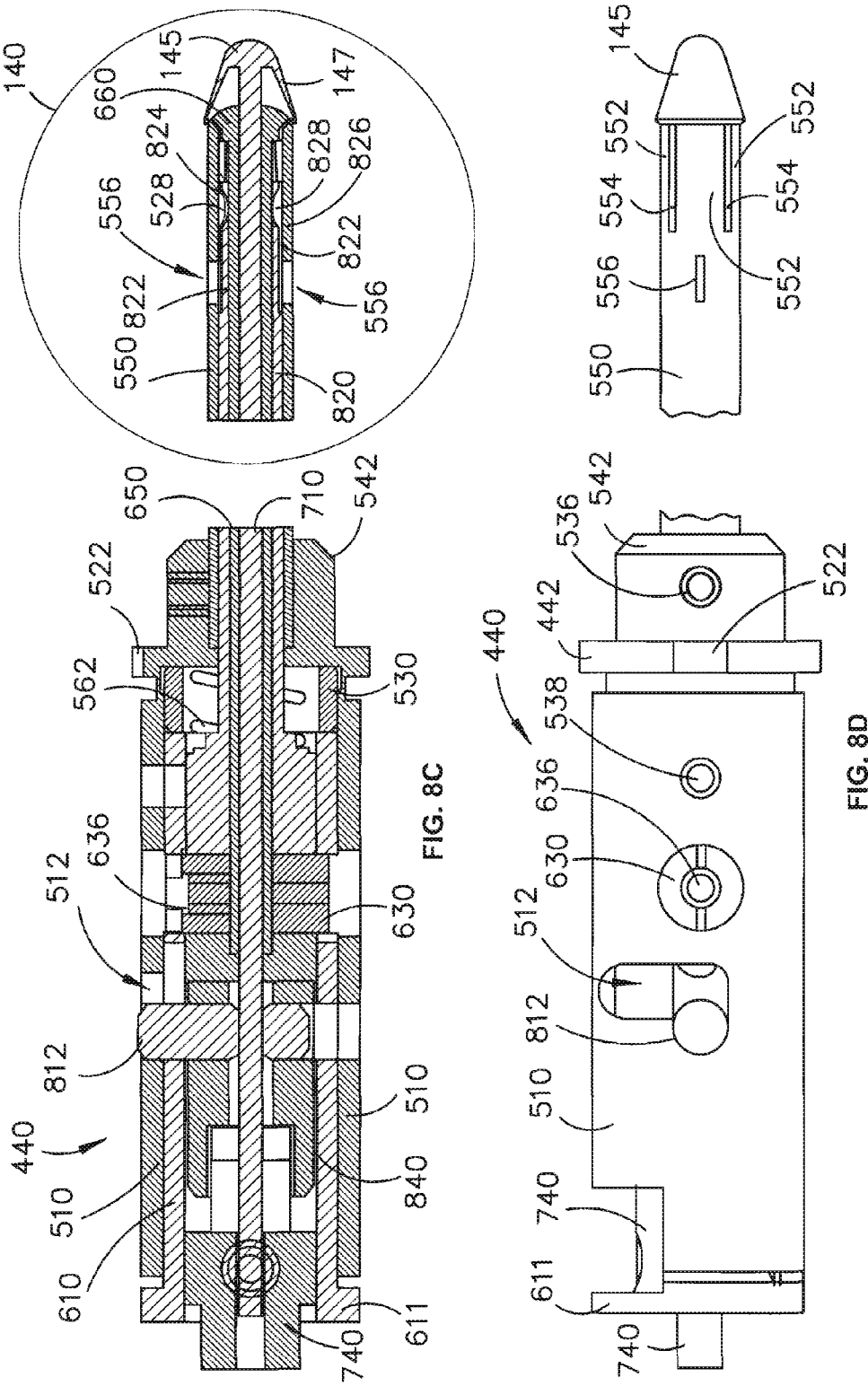

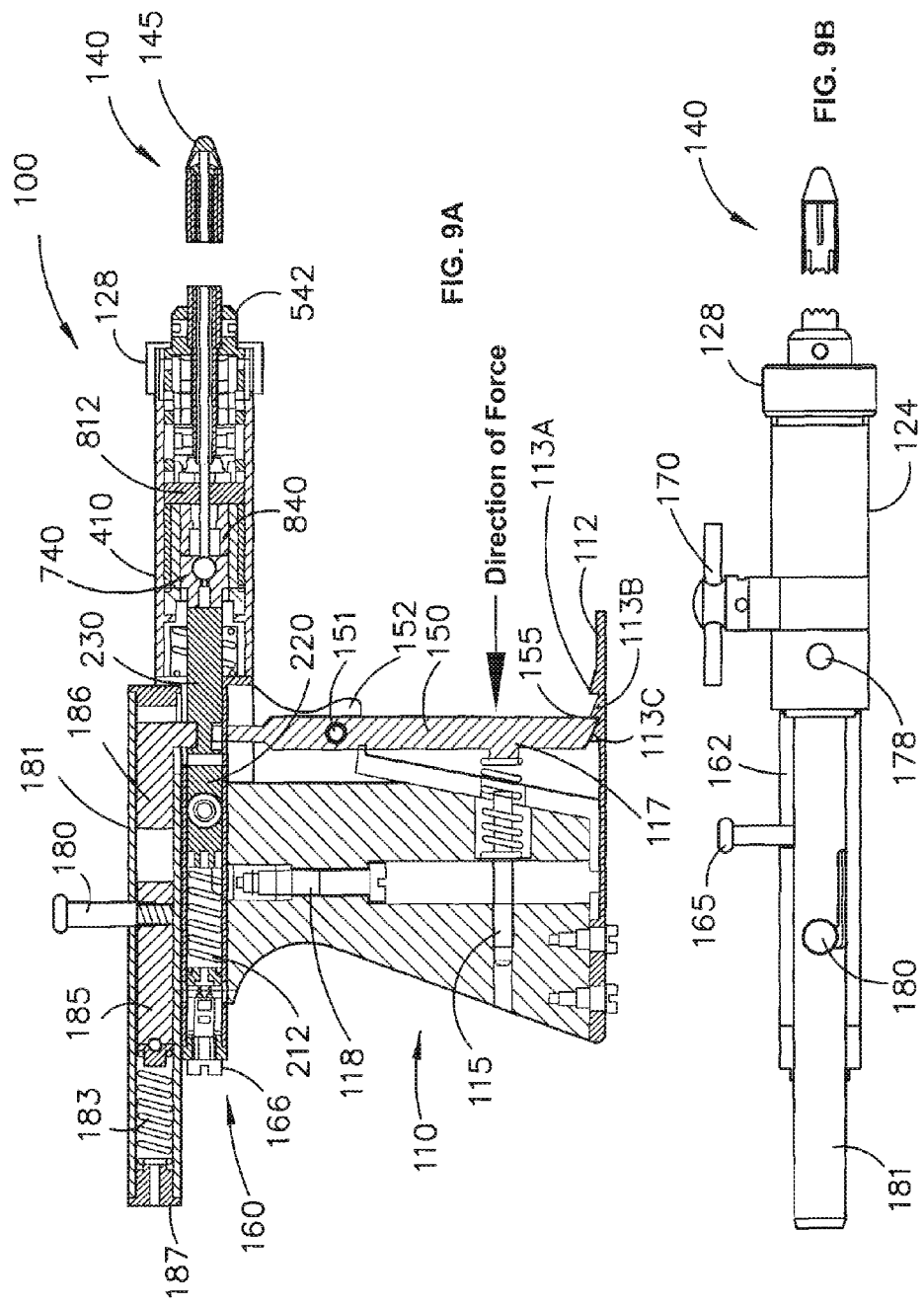

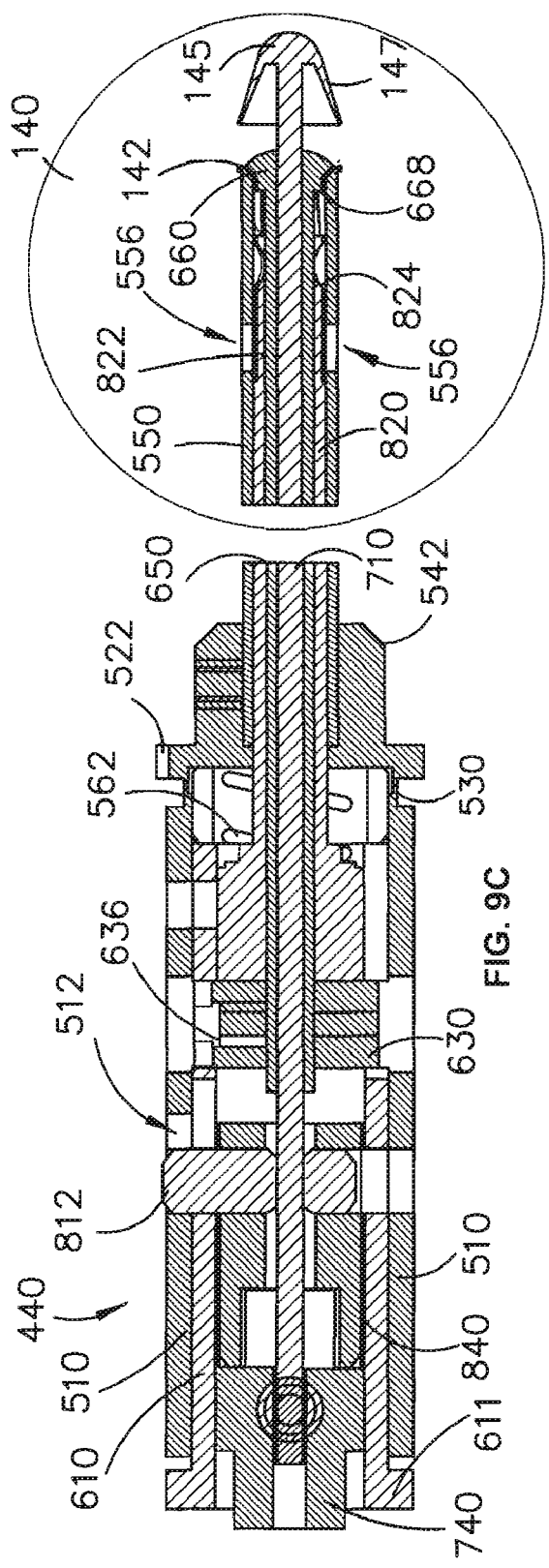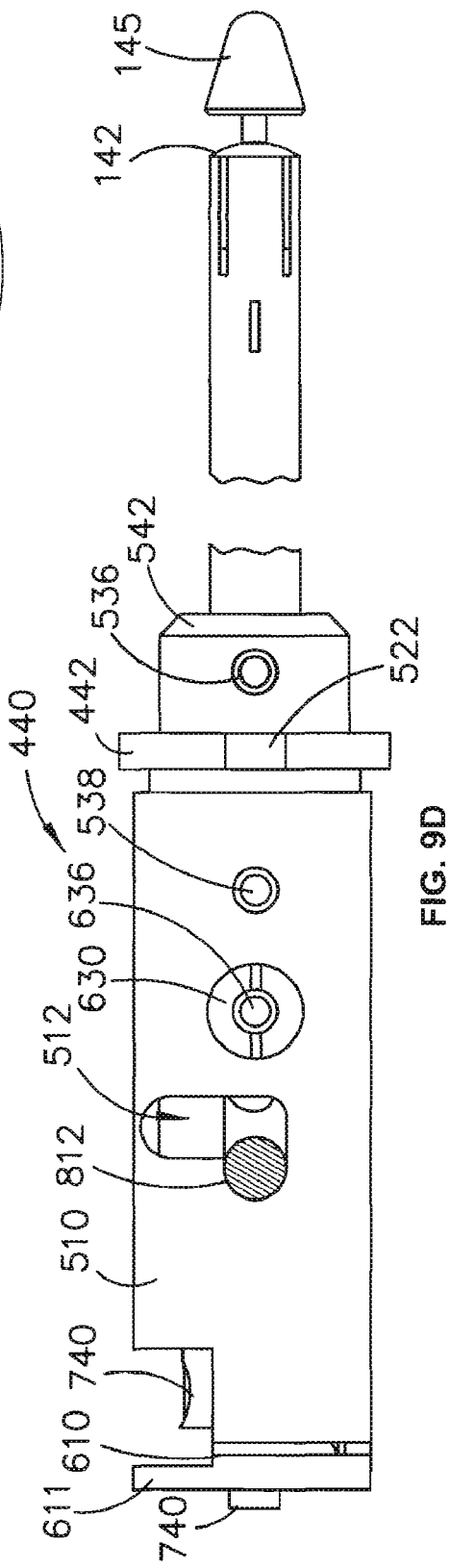

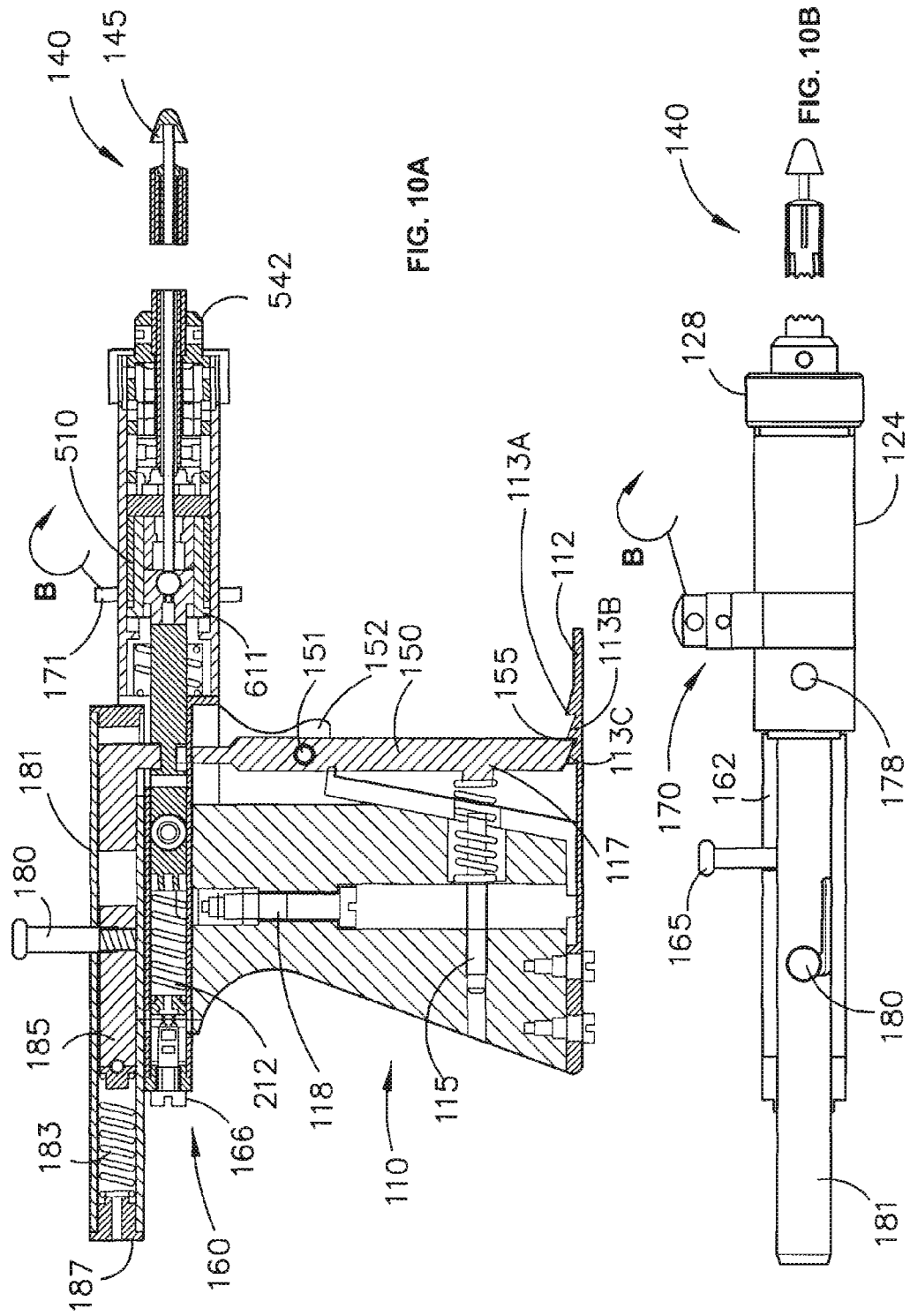

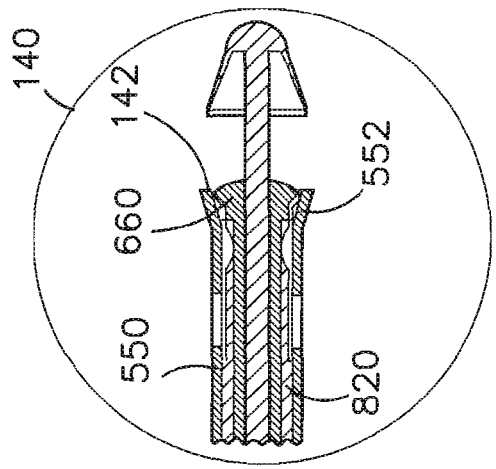
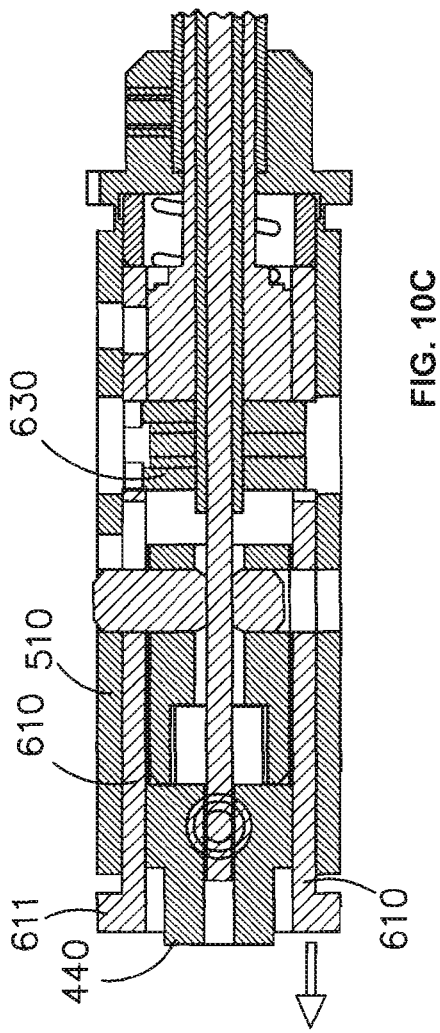
FIG. 10C
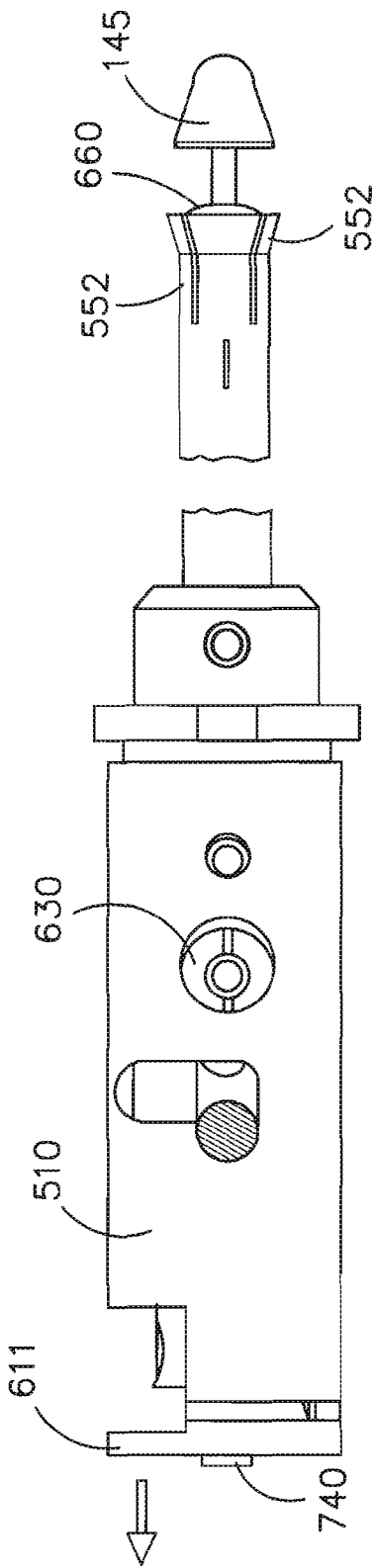
FIG. 10D

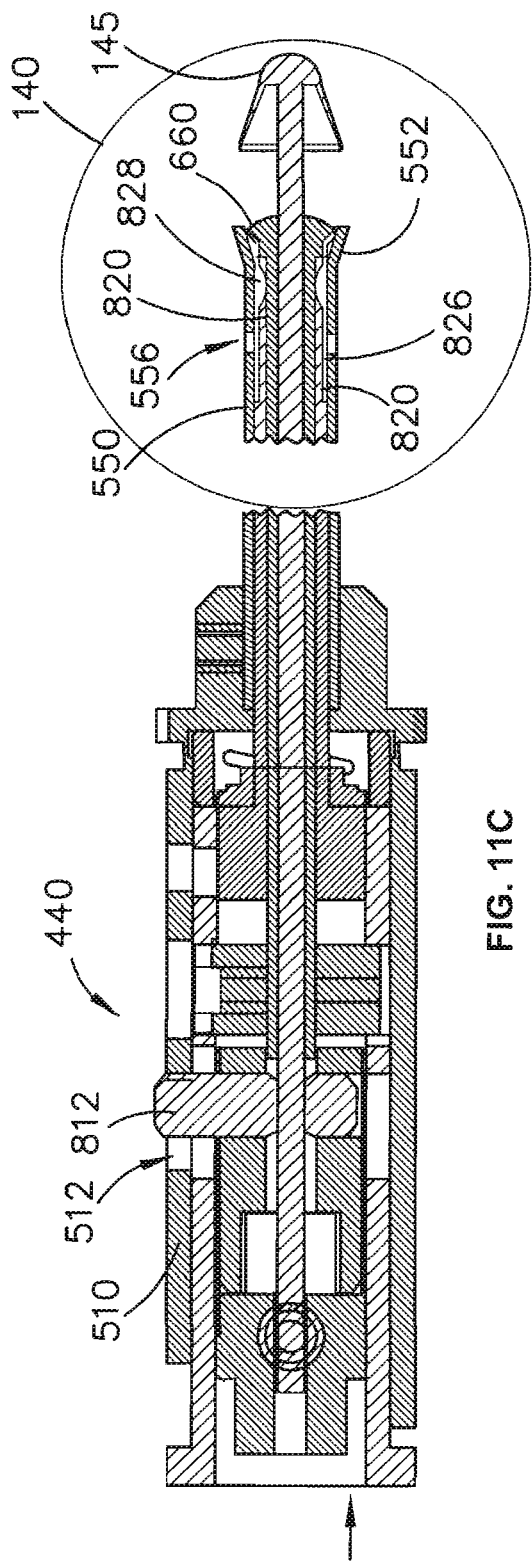
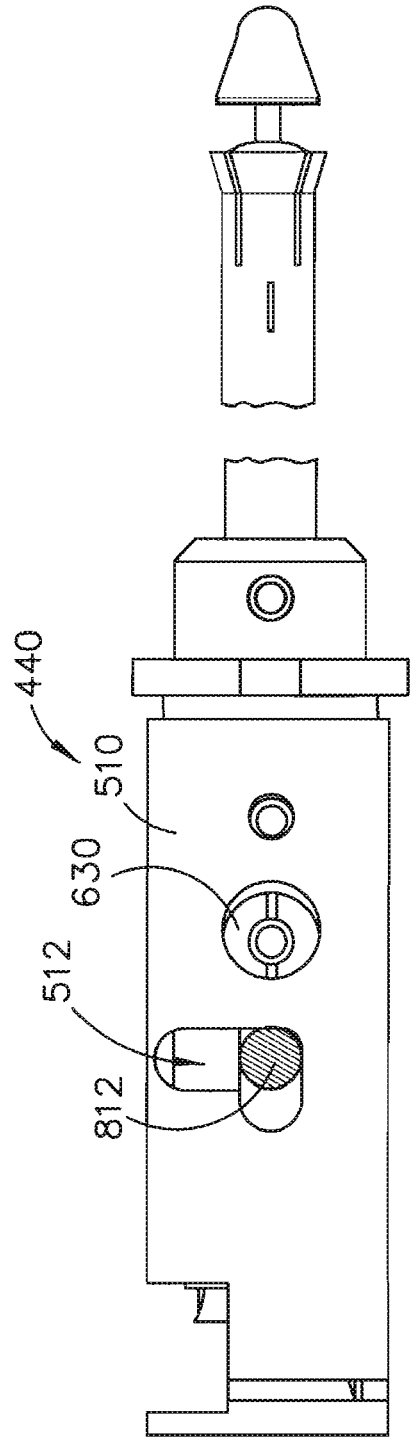
FIG. 11C
FIG. 11D

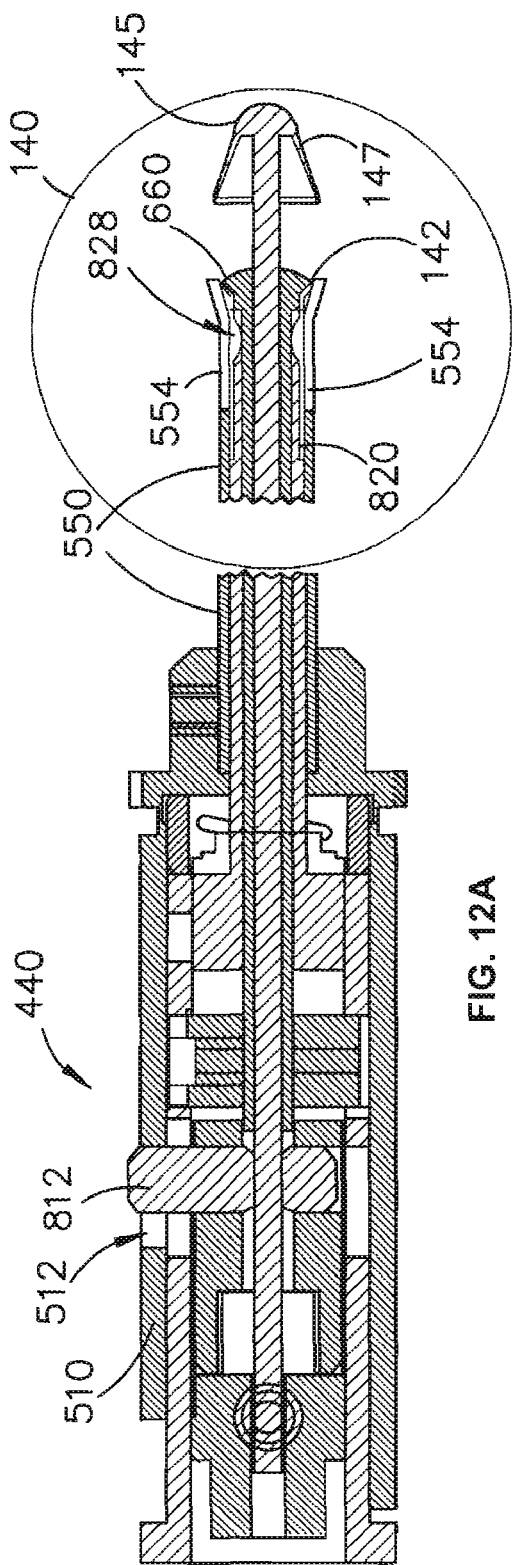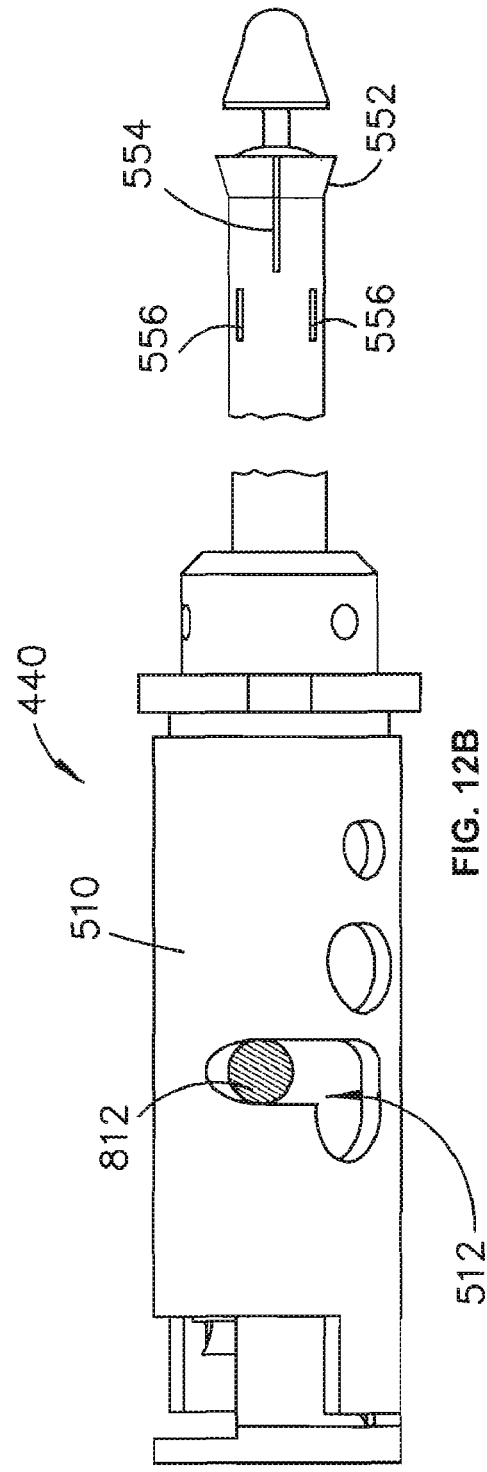

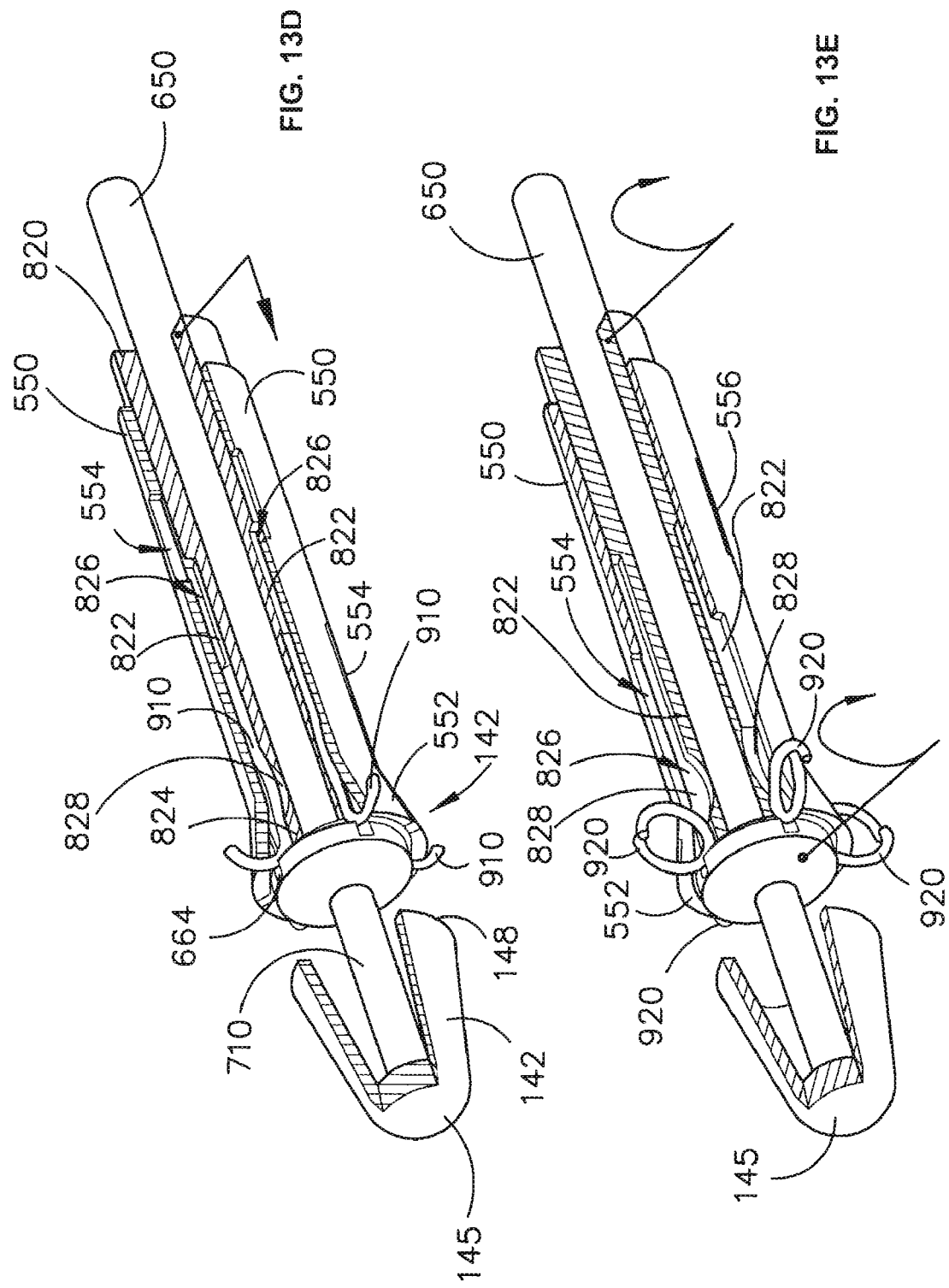

DEVICE AND METHOD FOR DELIVERING SHAPE-MEMORY STAPLES

CROSS REFERENCE TO RELATED APPLICATIONS

This application claims the benefit of U.S. provisional patent application Ser. No. 61/162,462, filed 23 Mar. 2009, and is a continuation-in-part of International Application no. PCT/AU2008/000623, filed 2 May 2008, which claims priority to Australian provisional patent application no. 2007902314, filed 2 May 2007, the entire disclosure of each of which is hereby incorporated by reference.

TECHNICAL FIELD

The described embodiments relate generally to methods and devices for delivering shape-memory staples. According to some embodiments, the delivered shape-memory staples can be used for securing a graft to another body.

BACKGROUND

In some types of surgery, it can be advantageous to use staples to affix tissue or grafts to other tissues or grafts. Such staples can serve to keep the tissues and/or grafts together while the body heals or undergoes treatment.

Not all medical stapling devices are effective or optimal for each situation in which deployment of staples may be necessary or desirable.

The described embodiments address or ameliorate one or more shortcomings or disadvantages associated with previous devices and/or methods for delivering shape-memory staples or at least provide a useful alternative thereto.

SUMMARY

Some embodiments relate to an apparatus comprising:

a plurality of chambers for receiving an associated plurality of staples, each formed with a shape memory that allows the staple to adopt a straightened configuration, when placed in a stapler, and a deployed configuration for suturing when released from the stapler; and a sleeve moveable relative to the chambers between a first position, in which the staples are trapped by the sleeve within the chambers in the straightened configuration, and a second position, whereby the staples are freed to adopt the deployed configuration, wherein the sleeve is adapted to move between the first and second positions by rotating relative to the chambers.

Some embodiments relate to a device for delivering shape-memory staples, the device comprising:

a handle formed as a pistol grip;

a trigger actuator coupled to the handle;

a drive mechanism coupled to the trigger actuator and the handle; and a delivery portion coupled to the drive mechanism, the delivery portion comprising retention walls for retaining the staples within the delivery portion in an elastically deformed configuration and release apertures for releasing the staples to adopt a deployed configuration based on their shape memory, wherein the delivery portion is configured to cause one end of each staple to protrude from the delivery portion in response to actuation of the trigger actuator.

Some embodiments relate to a device for delivering shape memory staples, the device comprising:

a grippable portion;

a delivery portion coupled to the grippable portion, the delivery portion comprising retention walls for retaining the staples within the delivery portion in an elastically deformed configuration and release apertures for releasing the staples to adopt a deployed configuration based on their shape memory, wherein the delivery portion is configured to cause one end of each staple to protrude from the delivery portion in response to actuation of the first actuator; and a head portion positioned at a tip of the delivery portion, the head portion being retractable in a proximal direction to cause the tip to flare outwardly.

BRIEF DESCRIPTION OF THE DRAWINGS

Embodiments are described hereinafter in further detail and by way of example, the detailed description of which should be read in conjunction with the accompanying drawings, in which:

FIG. 6 is an exploded perspective view of the actuator clutch, showing an inner clutch sleeve and expander rod in further detail;

FIG. 8A is a side cross-sectional view taken along a vertical centre line of the device of FIG. 1, showing the device in an unactuated state;

FIG. 8B is a plan view of the device in the unactuated state, as shown in FIG. 8A;

FIG. 8C is a cross-sectional view of the actuator clutch and delivery portion, taken along a vertical centre line similar to FIG. 8A;

FIG. 8D is a plan view of the actuator clutch and delivery portion corresponding to FIG. 8C;

FIG. 9A is a side cross-sectional view taken along a vertical centre line of the device of FIG. 1, showing the device in a partially actuated state;

FIG. 9B is a plan view of the device in the partially actuated state shown in FIG. 9A;

FIG. 9C is a cross-sectional view of the actuator clutch and the delivery portion, taken along a vertical centre line similar to FIG. 9A, shown with the device in the partially actuated state;

FIG. 9D is a plan view of the actuator clutch and delivery portion corresponding to the partially actuated state in FIG. 9C;

FIG. 10A is a side cross-sectional view taken along a vertical centre line of the device of FIG. 1, showing the device in a further actuated state;

FIG. 10B is a plan view of the device as shown in FIG. 10A in the further actuated state;

FIG. 10C is a cross-section of the actuator clutch and delivery portion, taken along a vertical centre line similar to FIG. 10A, showing the actuator clutch and delivery portion in the further actuated state;

FIG. 10D is a plan view of the actuator clutch and delivery portion shown in the further actuated state;

FIG. 11C is a cross-sectional view of the actuator clutch and deliver portion, taken along a vertical centre line similar to FIG. 11A, showing the actuator clutch and delivery portion in the still further actuated state;

FIG. 11D is a plan view of the actuator clutch and delivery portion in the still further actuated state;

FIG. 12A is a side cross-sectional view of the actuator clutch and delivery portion, taken along a plane angularly offset from the vertical centre line of the device, showing the actuator clutch and delivery portion in a final actuation state;

FIG. 12B is a plan view of the actuator clutch and delivery portion shown in the final actuation state;

FIG. 13D is a partial cutaway perspective view of the delivery portion, with the device in a further partially actuated state;

FIG. 13E is a partial cutaway perspective view of the delivery portion, with the device shown in the final actuation state;

Like reference indicators as between the drawings are intended to indicate like elements, features or functions. The drawings are not to scale and should be considered to be exemplary, for the purposes of illustrating features and functions of the described embodiments.

DETAILED DESCRIPTION

Figure 1:
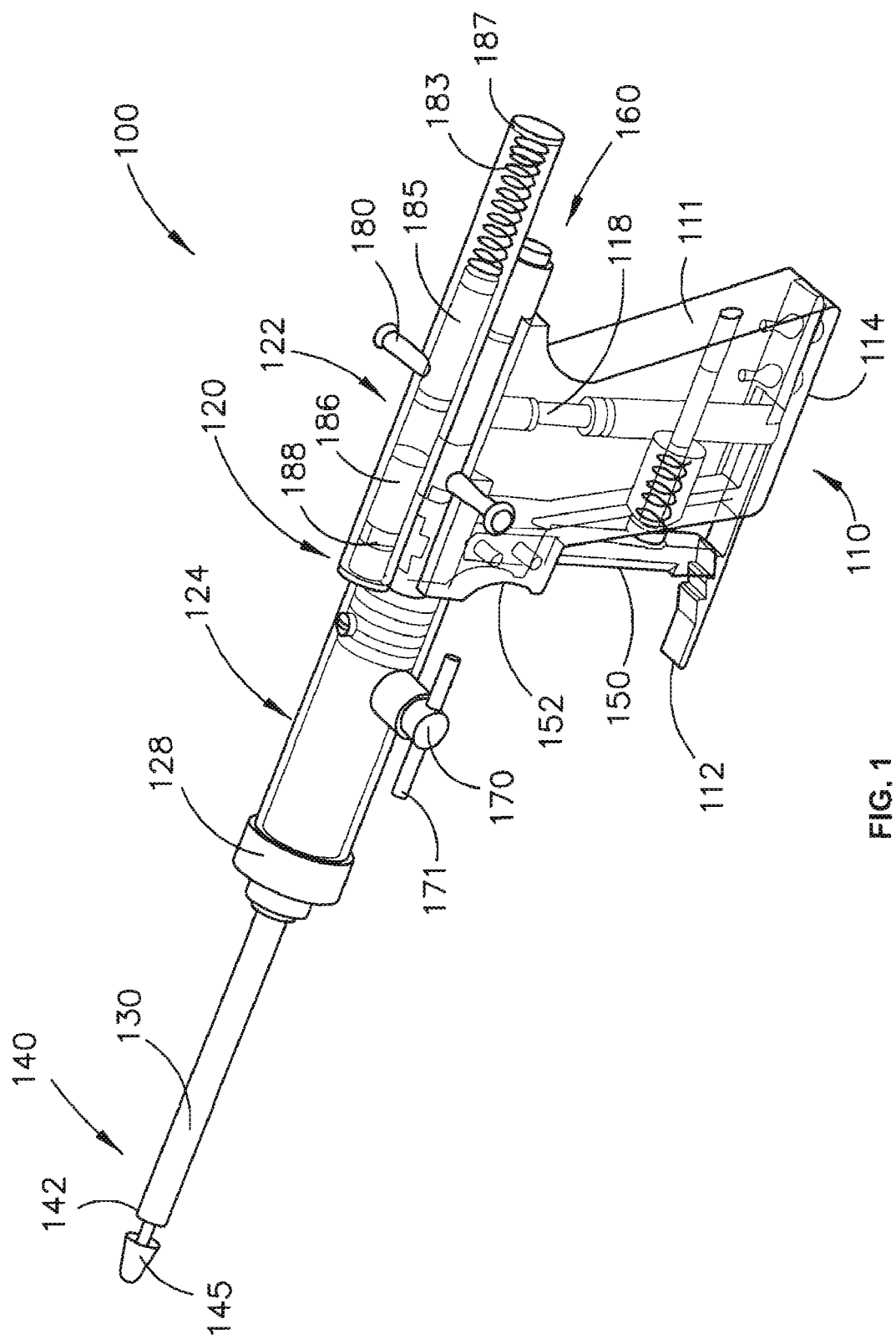
FIG. 1 is a perspective view of a device for delivering shape-memory staples.

The described embodiments relate generally to devices for delivering shape-memory staples 910 and staple delivery methods performed using such devices. In some embodiments, a staple delivery device 100 comprises a striking mechanism 190 for delivering a striking blow to cause ends of the staples 910 to protrude in a stabbing manner, thereby enabling the staples 910 to penetrate dense and/or hardened substances surrounding the staple delivery site.

In other embodiments, release apertures 554 for releasing the staples 910 from a delivery portion 140 extend in a slight spiral relative to a longitudinal axis of the delivery portion 140. In still further embodiments, the device 100 comprises a somewhat bulb-shaped portion 660 positioned at a delivery end of the device 100 and configured to be axially withdrawn into the delivery end to cause a substantially cylindrical sheath 550 around the delivery end to slightly flare outwardly.

In some further embodiments, the device 100 may comprise a dome-shaped cap 145 at a distal end of the device 100 that is movable between a proximal position, in which an apron 147 at an open end 148 of the domed portion 145 fits around the cylindrical delivery tip 142, for example to hold a graft in place, where the graft is a substantially tubular graft fitting around at least part of the shaft 130 of the device 100, and a distal position. In the distal position, the dome-shaped cap 145 does not overlie the cylindrical end tip portion 142 and allows radial protrusion of one end of each staple 910 into the graft, in preparation for delivery of the staples to affix the graft to another body.

Embodiments of the device are shown and described in relation to Figures I to 15, by way of non-limiting example. As shown in FIG. 1, device 100 includes a grippable handle 110 having a palmar grip 111, a ratchet 112, a depressible trigger 150 and a finger grip portion 152. When device 100 is held in a hand, grippable handle 110 is shaped to accommodate palmar grip 111 in a palm and/or thenar area of the hand, with fingers extending around trigger 150 and finger grip portion 152 so that device 100 can be firmly held and operated. Trigger 150 is movable relative to ratchet projections 113a, 113b and 113c by squeezing the third, fourth and fifth fingers of the hand, for example. Ratchet 112 cooperates with an angled trigger foot 155 at the base of trigger 150, which acts as a ratchet engagement portion, to hinder outward movement of trigger 150 relative to a main body of handle 110. Trigger foot 155 can be actuated to successively engage ratchet projections 113a, 113b and 113c, with ratchet projection 113a maintaining trigger 150 in an unactuated state.

Trigger 150 is pivotable relative to finger grip portion 152 of handle 110 about an axis defined by a trigger pivot pin 151 received in a pin hole 153 formed in the finger grip portion 152. Trigger 150 has a split claw 154 formed at an opposite end to trigger foot 155 to engage a proximal drive mechanism 160 described below.

Figure 2:
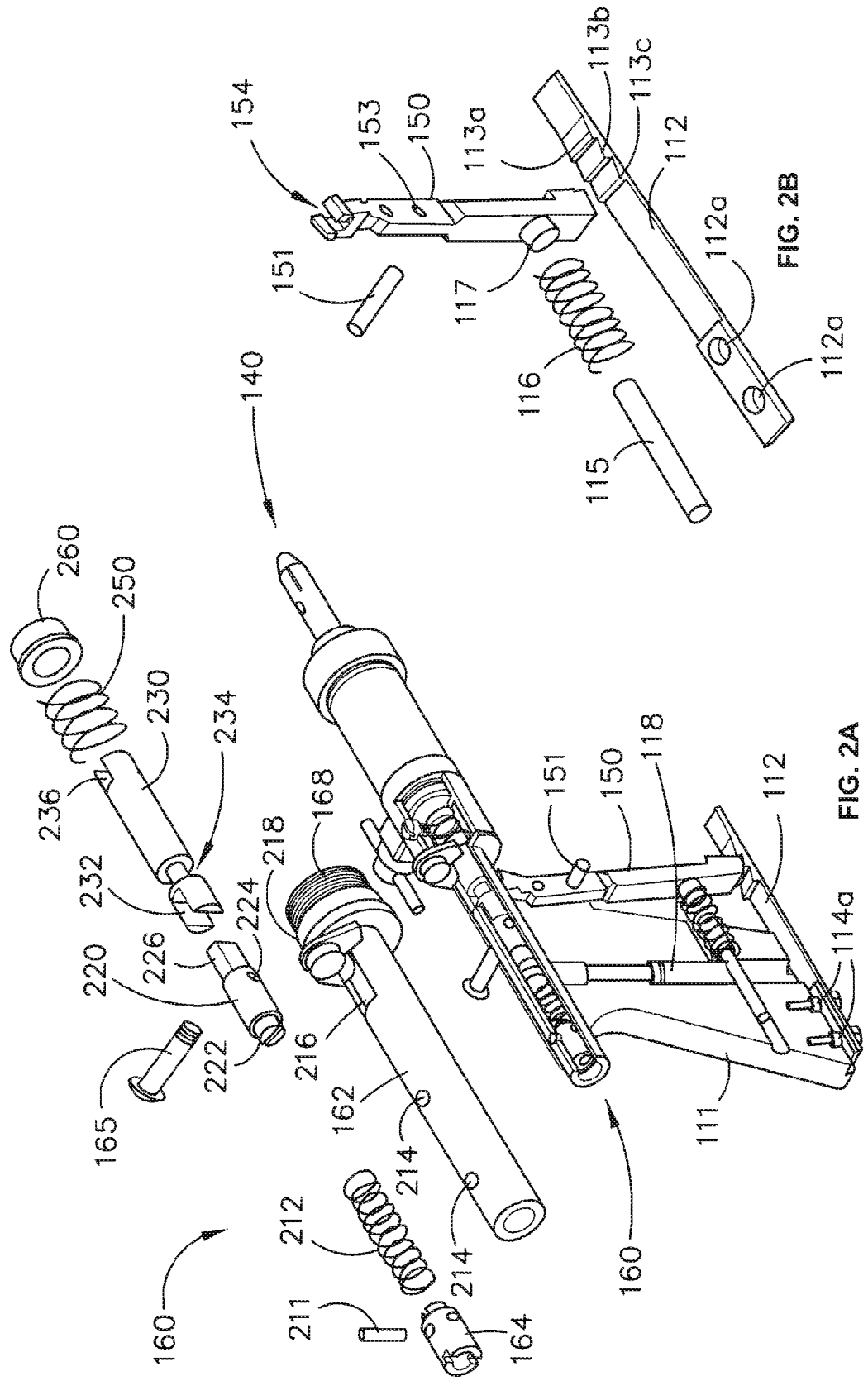
FIG. 2A is an exploded perspective view of the device of FIG. 1, showing a proximal drive mechanism in further detail.
FIG. 2B is an exploded perspective view of part of an actuation mechanism of the device of FIG. 1.

As shown in FIGS. 2A and 2B, handle 110 further comprises a movement limiting bolt 115 positioned in a body of the handle 110 to limit inward movement of trigger 150. A spring 116 is positioned around movement limiting bolt 115 and is at least partially received within the body of the handle 110 at one end and positioned around a spring registration boss 117 formed on an inner face of trigger 150. Spring 116 serves to bias trigger 115 outwardly, so that trigger foot 155 sits against a ratchet projection 113a, 113b or 113c. Handle 110 also houses a retention bolt 118 to affix the proximal drive mechanism 160 to handle 110.

Ratchet 112 is preferably formed of a flexible spring steel. Ratchet 112 may be secured to a base 114 of handle 110 by base bolts 114a received through ratchet apertures 112a at one end of ratchet 112. Ratchet projections 113a, 113b and 113c are formed at an opposite end to apertures 112a and ratchet 112 is sufficiently flexible so that trigger 150 can be moved outwardly past one or more ratchet projections 113a, 113b or 113c (to reset trigger 150 after actuation) when ratchet 112 is resiliently deflected downwardly away from the body of handle 110.

Handle 110 is coupled to an actuation portion 120 which comprises a proximal actuation portion 122 and a distal actuation portion 124. A shaft 130 is coupled to distal actuation portion 124 to communicate actuation movements and forces to a delivery portion 140 positioned at a distal end of device 100.

In the context of this description, positional references are used, assuming that device 110 will be held in the manner of a pistol, with base 114 being oriented generally downwardly and a "barrel" of the "pistol" extending generally outwardly. The relative term "proximal" should be interpreted to indicate a direction or position close to or toward a palm of the hand when the hand is positioned around handle 110 in the intended manner previously described. The term "distal" is intended to indicate a direction or position opposite to "proximal", which will generally be away from the hand gripping handle 110. These and other positional references are provided for ease of understanding only and are not intended to limit the actual position or orientation of the device during use.

Proximal actuation portion 122 includes proximal drive mechanism 160 and a striking mechanism actuable by a striking actuator 180.

As shown in FIG. 2A, proximal drive mechanism 160 comprises a proximal drive sleeve 162 coupled to and resting against a top of handle 110. Proximal drive sleeve 162 has a proximal end insert 164 received through an open proximal end of sleeve 162. An insert locator pin 211 is received through a correspondingly sized aperture in proximal end insert 164 and through radial aperture 214 formed in proximal drive sleeve 162. Insert locator pin 211 remains partially received in radial aperture 214 to fix proximal end insert 164 in position within sleeve 162. A drive spring 212 is also positioned within sleeve 162 so as to have one end of the spring positioned against an internal boss on proximal end insert 164. Spring 212 is positioned partially around a projecting boss of a proximal end 222 of a first clutch portion 220 that is also received within proximal drive sleeve 162. Spring 212 serves to bias first clutch portion 220 in a distal direction.

Proximal drive sleeve 162 partially houses a second clutch portion 230 that has a further slotted end 232 shaped to mate with a keying end 226 of the first clutch portion 220. Second clutch portion 230 has a neck portion 234 positioned intermediate first slotted end 232 and a second slotted end 236. Neck portion 234 is shaped to partially meet and engage with split claw 154 of trigger 150 so that proximal actuation of trigger 150 (i.e. by squeezing the fingers of the hand) causes distal movement of split claw 154, which engages second clutch portion 230 around neck portion 234 to cause second clutch portion 230 to move distally within proximal drive sleeve 162.

A staple release actuator 165, generally formed as a projecting lever and indicated as "Lever D" in the drawings is coupled to first clutch portion 220 by a screw threaded coupling through threaded hole 224 formed in first clutch portion 220. A moment applied to staple release actuator 165 causes rotation of first clutch portion 220 about a longitudinal axis of device 100. This rotational movement of first clutch portion 220 causes like rotational movement of second clutch portion 230, which in turn causes like rotation of a drive clutch 740 (described in further detail below) to move part of delivery portion 140 relative to outer delivery sleeve 550 (where permitted by the positioning of release actuator limiting rod 812 within release actuator limiting channel 512, as described below).

Figure 4:
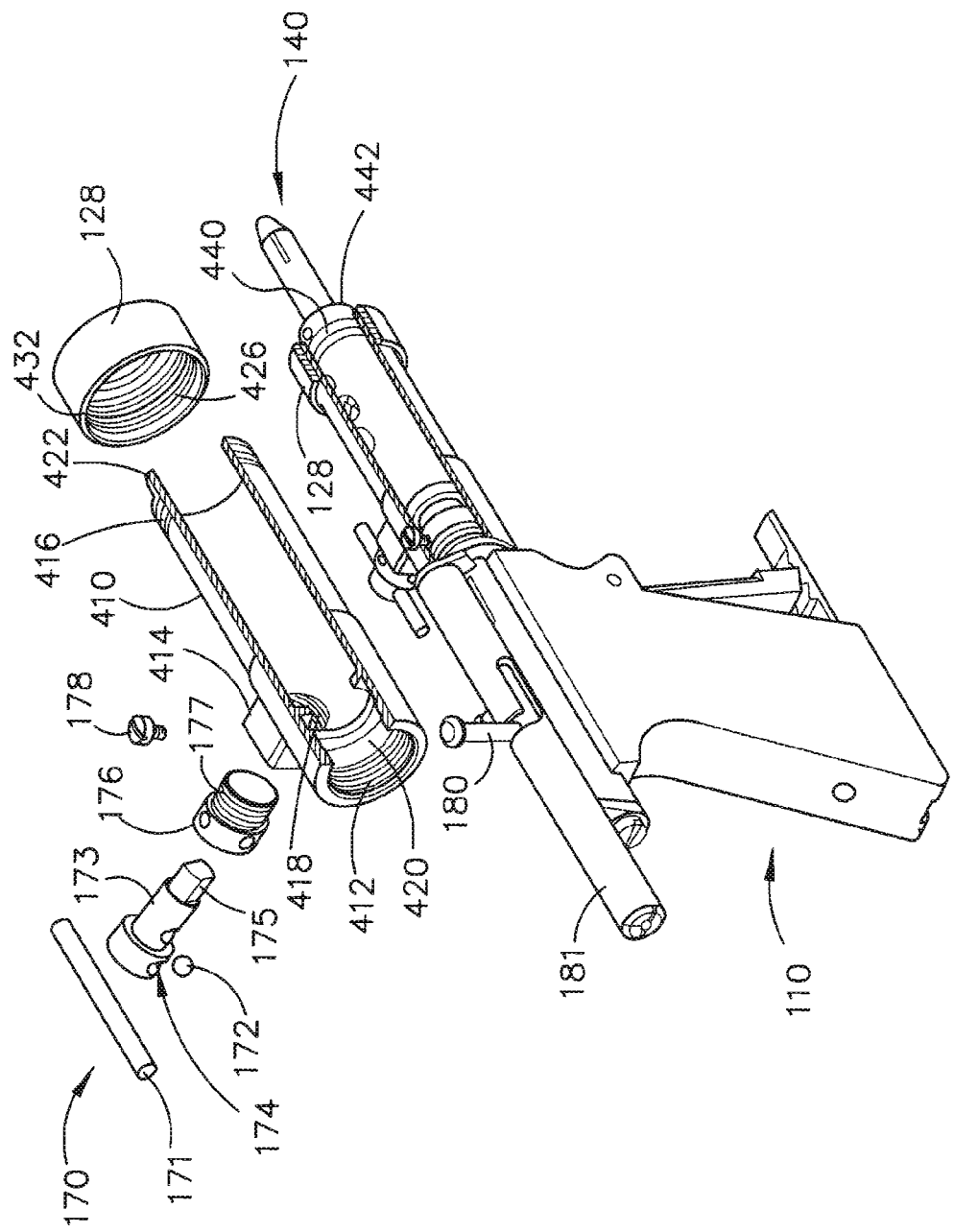
FIG. 4 is an exploded perspective view of the device of FIG. 1, showing a head retraction actuator and barrel in further detail.

Proximal drive sleeve 162 has an enlarged distal end with a male threaded cylindrical wall 218 for threaded engagement with barrel housing 410 (FIG. 4). A top screw 178 is insertable through a screw-receiving aperture 418 in barrel housing 410 and into a threaded aperture 168 formed in the distal end of proximal drive sleeve 162 to fix barrel housing 410 to proximal drive sleeve 162.

A spring 250 and positioning element 260 are received in the distal end of proximal drive sleeve 162 and in the proximal end of barrel housing 410 to receive and position second slotted end 236 relative to a clutch head portion 742 of drive clutch 740.

Proximal drive sleeve 162 has a slotted aperture 216 formed toward a distal end of sleeve 162 to receive a striking transmission portion 188 of anvil 186 therethrough. Striking transmission portion 188 is configured to project downwardly from within a generally cylindrical striking actuator housing 181 through slotted aperture 216 to be received in neck portion 234. Opposed claws of split claw 154 may be sized to fit around the reduced diameter portion of neck portion 234 and to at least partially receive a lower extremity of striking transmission portion 188. Thus, movement of either of anvil 186 and trigger 150 causes movement of second clutch portion 230 along its longitudinal axis.

Figure 3:
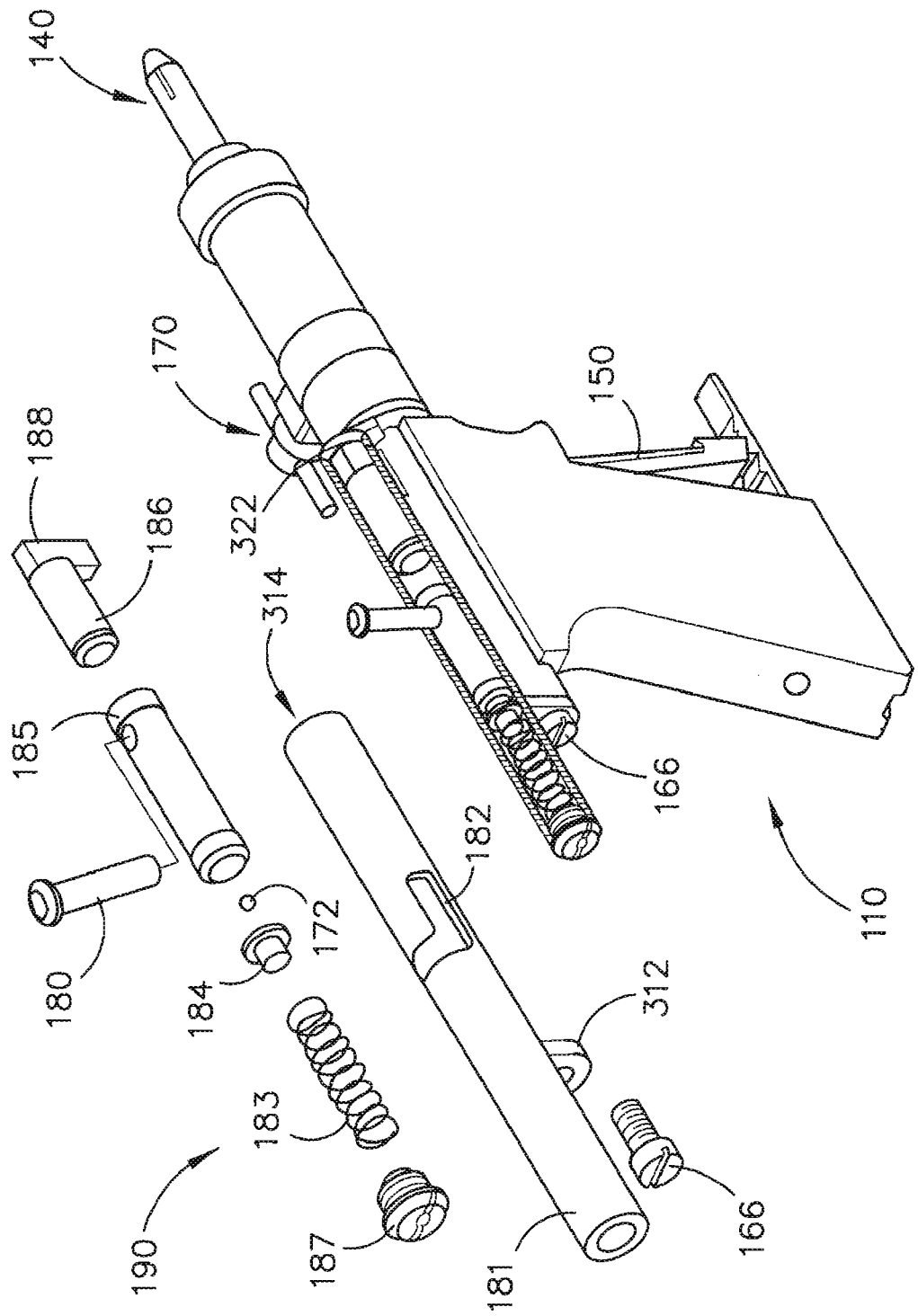
FIG. 3 is an exploded perspective view of the device of FIG. 1, showing a striking mechanism in further detail.

As shown in FIG. 3, striking mechanism 190 comprises a striking piston 185 axially movable within striking actuator housing 181 (formed as a hollow cylinder) to act as a hammer upon anvil 186 under the action of a striking actuator spring 183 proximally positioned within housing 181. A striking actuator 180, formed as a lever, and shown in the drawings as "Lever C", may be coupled to striking piston 185 by means of screw-threaded engagement. Striking actuator 180 extends radially through an L-shaped guide channel 182 formed in housing 181. Part of guide channel 182 extends circumferentially to allow for rotational movement of striking actuator 180 and striking piston 185 within housing 181. However, housing 181 also defines a longitudinal section of guide channel 182 that permits striking actuator 180 to move longitudinally within that section of guide channel 182.

One end of spring 183 is positioned against an end cap 187 secured at a proximal end of housing 181, for example by screw threaded engagement. The other end of spring 183 acts on an inner cap 184 having a boss around which fits the end of spring 183. Inner cap 184 abuts a proximal end of striking piston 185 so that, under the action of spring 183, striking piston 185 is biased in the distal direction.

When striking actuator 180 is in an unactuated position, it is received within the circumferential portion of guide channel 182, in which the part of striking actuator housing 181 that defines guide channel 182 hinders distal movement of striking actuator 180. In order to actuate striking actuator 180 (move it into an actuated position), striking actuator 180 may have a moment applied to rotate it toward the longitudinal section of guide channel 182 so that striking piston 185 and striking actuator 180 become free to move in the distal direction under the biasing action of spring 183.

Striking actuator housing 181 may be secured to proximal drive sleeve 162 by receipt of a proximal end screw 166 through an aperture formed in a downwardly pending positioning flange 312 formed on or attached to housing 181. A threaded end of proximal end screw 166 may be received in a matingly threaded proximal end of proximal end insert 164 in order to secure proximal end screw 166 in position and thereby assist in fixedly locating housing 181 on top of, and adjacent to, proximal drive mechanism 160. Axes of movement of the mechanisms within proximal drive mechanism 160 and striking mechanism 190 are generally longitudinal and parallel.

As an additional means of securing housing 181 relative to proximal drive sleeve 162, a distal end 314 of housing 181 is configured to mate with and receive a positioning boss 322 located toward a distal end of proximal drive sleeve 162. Positioning boss 322 is fixed relative to the cylindrical barrel of proximal drive sleeve 162 and is positioned to be slightly above a distal end of slotted aperture 216.

Referring also to FIG. 4, head retraction actuator 170 and barrel housing 410 are described in further detail. Head retraction actuator 170 comprises a bar 171 received within a bar receiving channel 174 defined by' a head portion of a rotation key 173. A ball 172 is received in an aperture formed in a shaft of rotation key 173 in order to fix bar 171 in position relative to channel 174. Rotation key 173 has a cam 175 on an inner end thereof for engaging and proximally shifting inner clutch sleeve 610 (FIG. 6) by a camming engagement of a distal face 611a of proximal end flange 611 of inner clutch sleeve 610. Rotation key 173 is received within registration barrel 176, which is received by screw-threaded engagement with actuator insert port 414 formed in one side of barrel housing 410. Registration barrel 176 has a male screw thread 177 for engaging with a corresponding female screw thread within actuator insert port 414.

Barrel housing 410 comprises a threaded proximal end 412 sized to fit around and engage with threaded cylindrical wall 218 of proximal drive sleeve 162. Barrel housing 410 also comprises an internal annular flange 420 within which sits positioning element 260. At its distal end, barrel housing 410 has a threaded distal end 416 from which upper and lower registration bosses 422 extend distally to register and mate with registration notches 522 formed at corresponding upper and lower positions on external annular flange 442 of actuator clutch 440.

A retention cap 128 slides over a distal end of actuator clutch 440 to retain actuator 440 within barrel housing 440. Retention cap 128 has an internal thread 426 to engage with threaded distal end 416 of barrel housing 410 and has an internal annular flange 432 to engage and abut a distal face of external annular flange 442, to thereby retain actuator clutch 440 within barrel housing 410. A distal opening in retention cap 128 allows a distal portion of actuator clutch 440 to extend therethrough, along with shaft 130.

Head retraction actuator 170, also shown in the drawings as "Lever B", can be partially rotated about a central axis of rotation key 173, which is normal to the longitudinal axis of device 100. This rotation causes retraction of a somewhat bulb-shaped expander head 660 within delivery portion 140, thereby causing delivery sleeve 550 to flare outwardly somewhat adjacent delivery tip 142.

It should be noted that the length of shaft 130 is depicted in FIGS. 2A, 3, 4, 5, 6, 7A and 7B as being quite short. This is done for ease of illustration only and does not represent the actual length of shaft 130. Rather, the relative length of shaft 130 as shown in FIG. 1 is intended to more accurately reflect the intended configuration of device 100, although it is to be noted that the drawings are not to scale.

Figure 5:
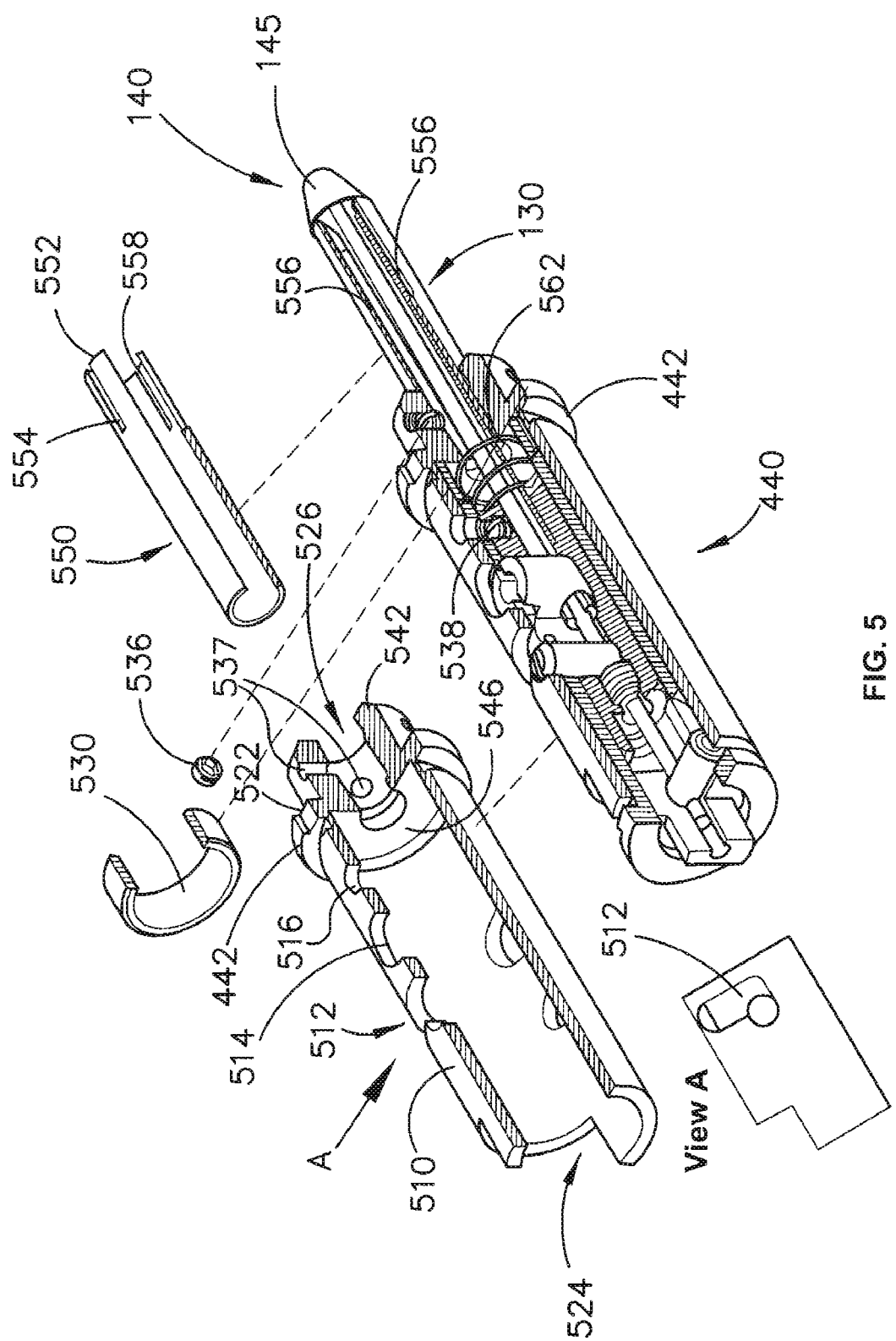
FIG. 5 is an exploded perspective view of an actuator clutch of the device, showing an outer clutch sleeve and delivery sleeve in further detail.
Figure 7A:
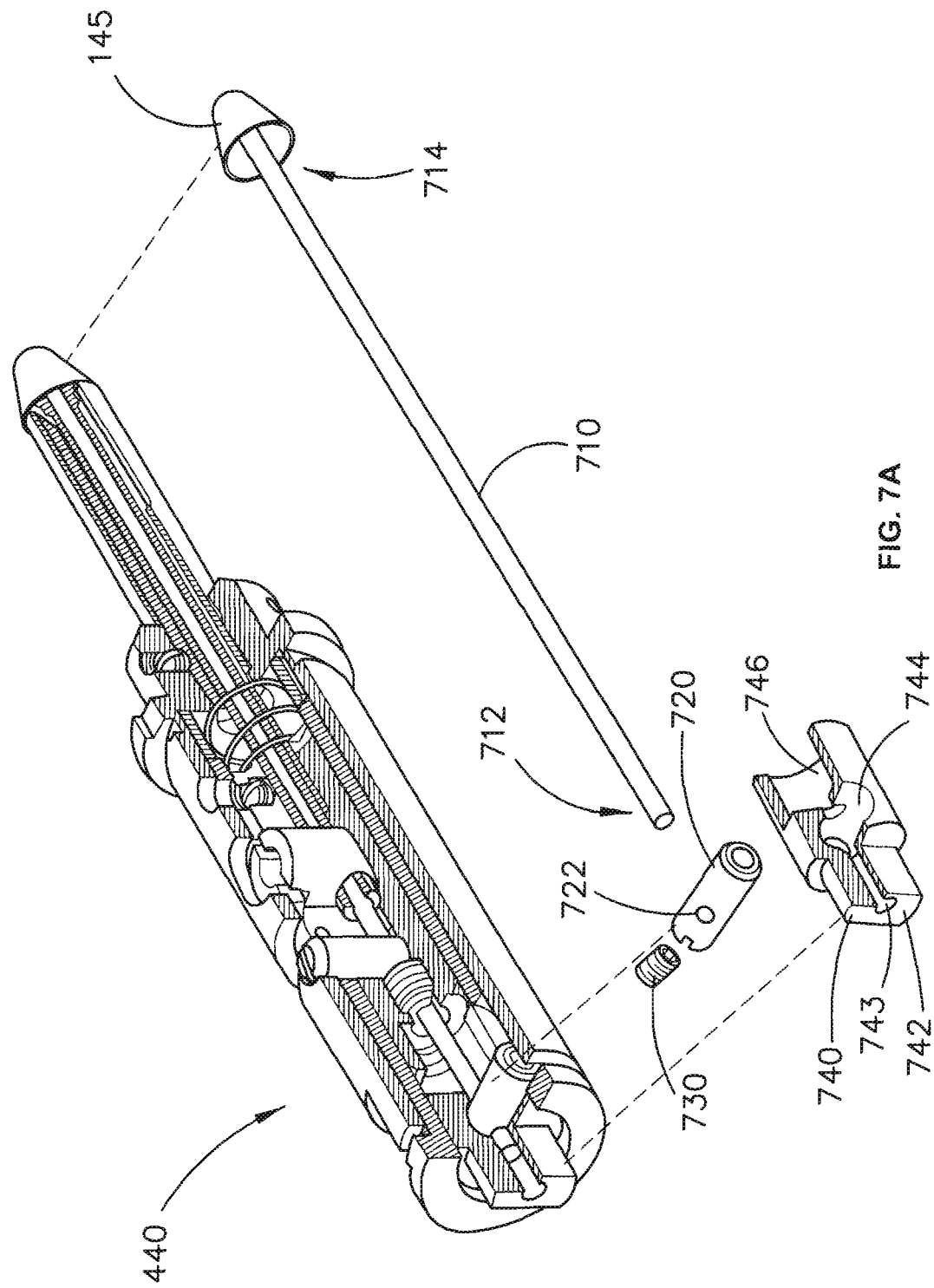
FIG. 7A is an exploded perspective view of the actuator clutch, showing a core rod and drive clutch in further detail.
Figure 7B:
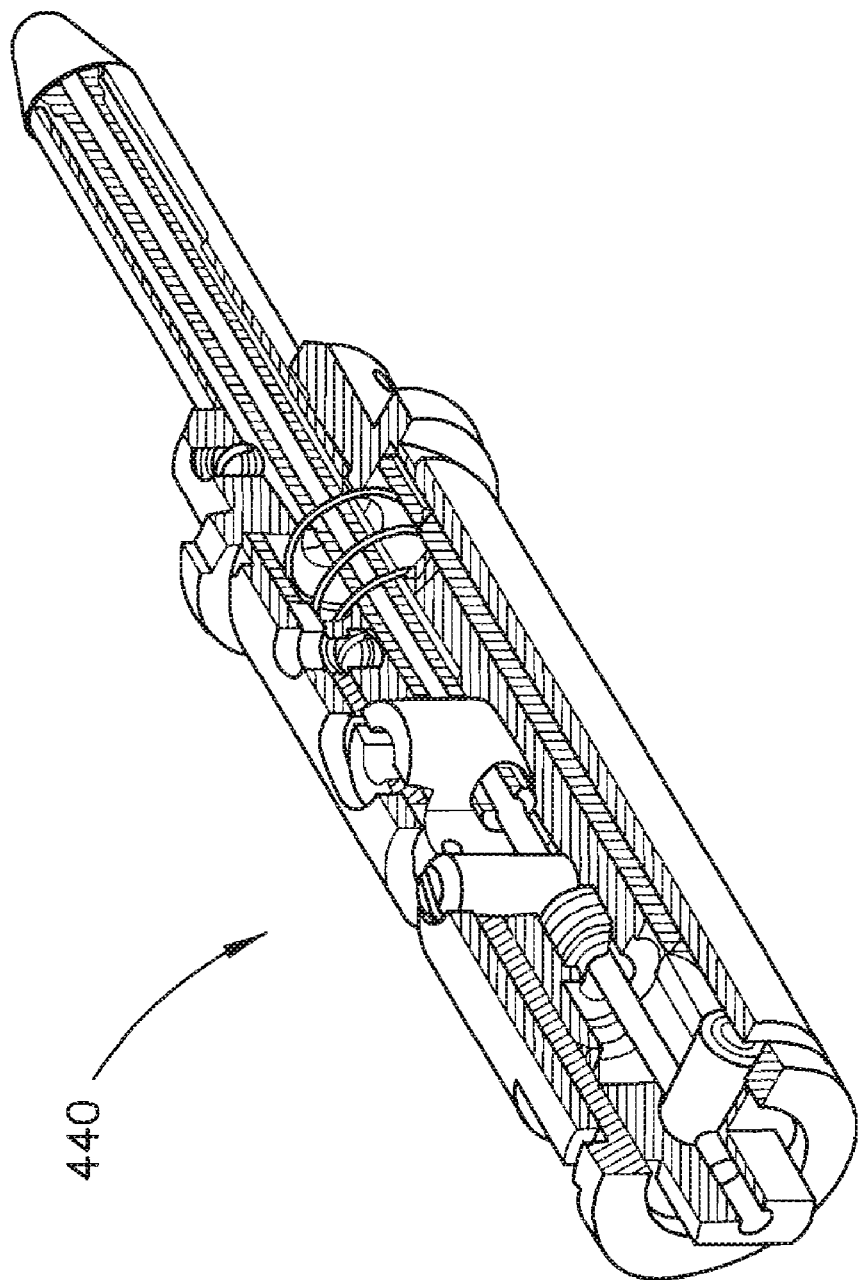
FIG. 7B is a perspective partial cutaway view of the actuator clutch, illustrating advancement of the core rod and drive clutch.
Figure 11A:
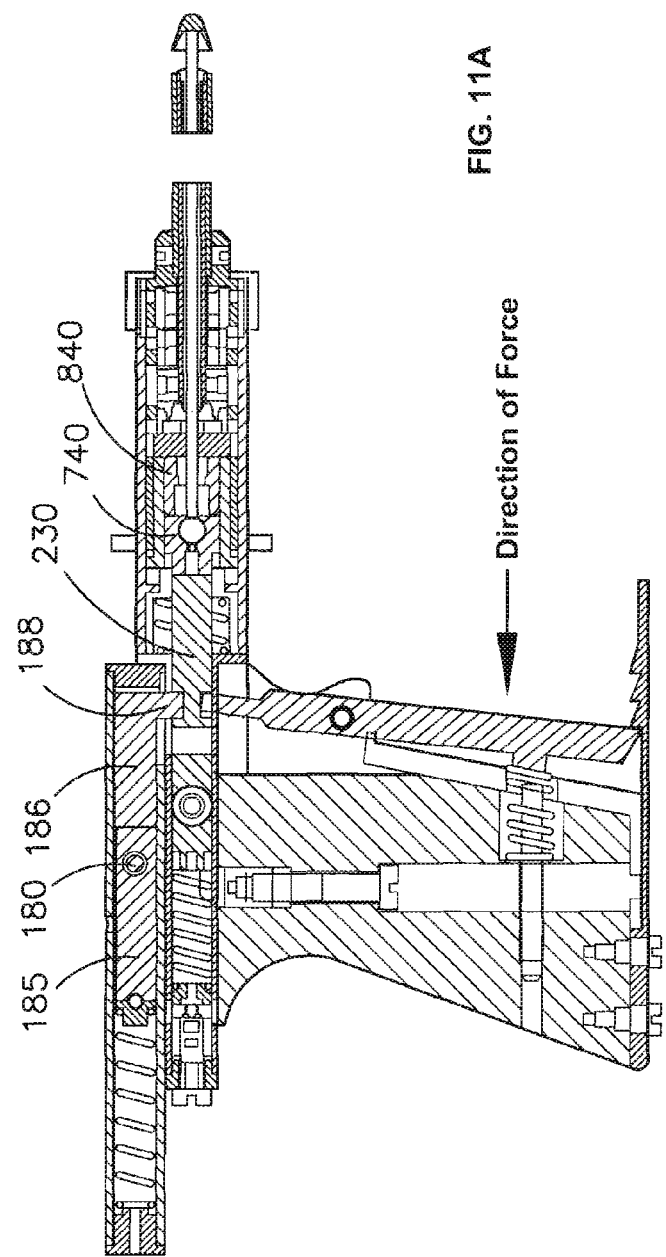
FIG. 11A is a side cross-sectional view taken along a vertical centre line of the device of FIG. 1, showing the device in a still further actuated state.
Figure 11B:
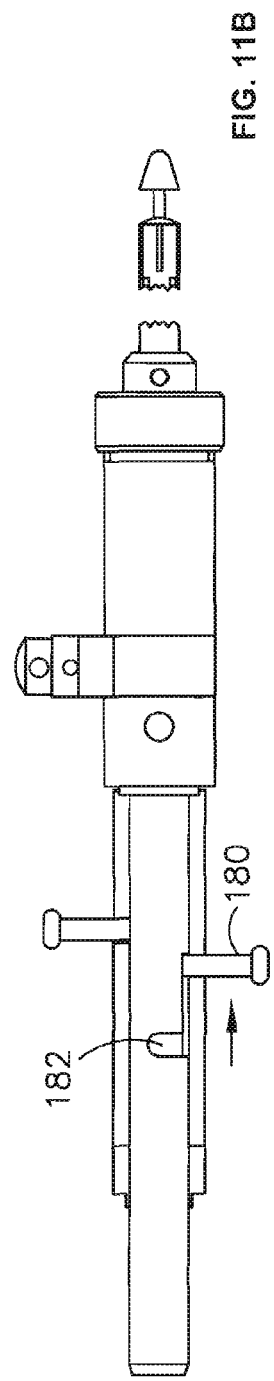
FIG. 11B is a plan view of the device in the still further actuated state shown in FIG. 11A.

Referring also to FIGS. 5 and 6, actuator clutch 440 is shown and described in further detail. Actuator clutch 440 comprises an outer clutch sleeve 510 and an inner clutch sleeve 610. Outer clutch sleeve 510 mostly surrounds inner clutch sleeve 610, except for a proximal end flange 611 which extends radially outwardly to an extent that it circumferentially coincides with an outer circumference of outer clutch sleeve 510. Outer clutch sleeve 510 and inner clutch sleeve 610 have radial apertures 514 and 614 to accommodate a locating cylinder 630 and radial screw apertures 516 and 616 to allow for insertion of a fixation screw 538 to affix inner delivery sleeve 820 an inner rotatable part of actuator clutch 440.

The generally cylindrical wall of outer clutch sleeve 510 defines a release actuator limiting channel 512, having a generally L-shaped configuration. Release actuator limiting channel 512 receives a head of release actuator limiting rod 812 therein in a manner such that channel 512 limits relative movement between outer clutch sleeve 510 and limiting rod 812. Limiting rod 812 is coupled to internal parts of actuator clutch 440 and is indirectly coupleable to proximal drive mechanism 160 as described below, and plays an important role in avoiding premature actuation of staple release actuator 165.

Outer clutch sleeve 510 has an outer sleeve proximal end opening 524, through which a proximal end of inner clutch sleeve 610 is received, and an outer sleeve distal end opening 526, through which a proximal portion of the shaft 130 extends. A distal end 542 of outer clutch sleeve 510 has a number of circumferentially spaced fixation apertures 537 for receiving fixation screws 536 to secure delivery sleeve 550 within outer sleeve distal end 542. Outer clutch sleeve 510 also defines an annular wall 546 toward distal end 542, against which a spring 562 and positioning ring 530 are located. Spring 562 serves to bias some internal components of actuator clutch 440 in the proximal direction. Spring 562 is positioned internally of positioning ring 530, which has approximately the same inner diameter as inner clutch sleeve 610.

The components of shaft 130 are generally coaxial with inner and outer clutch sleeves 610, 510, barrel housing 410 and proximal drive mechanism 160, although striking mechanism 190 is axially offset therefrom.

Distal actuation portion 124 includes head retraction actuator 170, barrel housing 410, actuator clutch 440, shaft 130 and delivery portion 140.

As shown in FIG. 5, outer delivery sleeve 550 has a proximal end received within outer sleeve distal end opening 526 and affixed to outer sleeve distal end 542 by fixation screws 536. At its distal end, outer delivery sleeve 550 has a number of release apertures 554, formed as generally longitudinally extending slots in the end of outer delivery sleeve 550. Release apertures 554 extend all the way to the distal extremity of outer delivery sleeve 550, thereby defining fingers 552 arranged in an interrupted cylindrical configuration. Fingers 552 define a generally angled inner profile at the distal opening of outer delivery sleeve 550 to accommodate engagement with a corresponding angled outer surface 662 of expander head 660. When expander head 660 is withdrawn slightly in the proximal direction, angled outer surface 662 engages and slides against angled inner profile 558 which, because fingers 552 are formed of a resiliently deflectable material, causes the fingers 552 to deflect slightly radially outwardly, thereby causing delivery tip 142 to flare outwardly. This outward flaring can assist in forcibly expanding vessel walls, for example, and can enable release of the staples at a radially increased position which, considering the generally circular shape memory of the staples, can lead to improved medical stapling quality.

Delivery sleeve 550 also defines insertion apertures 556 through which deformed (i.e. relatively straightened) staples can be inserted so as to be received within staple receiving chambers 826. Insertion apertures 556 may be formed as slots that are generally parallel to, but offset from, release apertures 556. Insertion apertures 556 are of a substantially shorter length than release apertures 554 and are positioned close to, but slightly proximally of, the proximal extremity of release apertures 554.

Inner clutch sleeve 610 defines a release actuator limiting channel 612 to permit movement of release actuator limiting rod 812 in proximal and distal directions, but not axially. When limiting rod 812 is allowed to move rotationally within limiting channel 512, limiting rod 812 causes inner clutch sleeve 610 to rotate along with limiting rod 812. This causes rotation of expander rod 650 to which inner clutch sleeve 610 is rotatably coupled by a locating cylinder 630. Specifically, expander rod 650 has its proximal end 652 received through a diametrical through hole 632 formed in locating cylinder 630. A fixation screw 636 is positioned axially within locating cylinder 630 to fix expander rod 650 relative to locating cylinder 630.

As shown in FIG. 6, expander head 660 is positioned at the distal end of expander rod 650 and has staple protrusion slots 664 extending in a generally axial but outward direction on the outside of expander head 660 to accommodate protrusion of staples 910 from within staple receiving chambers 826. Expander head 660 also has a shoulder 668 against which distal ends 824 of inner delivery sleeve 820 abut when inner delivery sleeve 820 is moved to its distal-most position. Angled outer surface 662 transitions from shoulder 668 to the radial and distal extremity of expander head 660, which generally positionally coincides with delivery tip 142.

Expander rod 650 comprises a generally hollow cylindrical wall 651 through which core rod 710 passes and is movable. Expander rod 650 is received within inner delivery sleeve 820, which is in turn received within outer delivery sleeve 550. Core rod 710 has a rod proximal end 712 and a rod distal end 714. Distal end cap 145 is positioned at the distal end 714. Distal end cap 145 may comprise a flexible medical grade plastic apron 147 extending proximally from the distal extremity of distal end cap 145. Apron 147 is intended to have enough firmness to hold a graft onto distal tip 142 in the unactuated position.

Proximal end 712 of core rod 710 is received within a diametrical through-hole 722 of a locating cylinder 720. Core rod 710 is affixed to locating cylinder 720 by a fixation screw 730 axially received within locating cylinder 720. Core rod 710 extends through diametrical through-hole 722 to be at least partially received within a central bore 743 of drive clutch 740. Drive clutch 740 also has a transverse bore 744 to accommodate locating cylinder 720. This arrangement is such that, when second clutch portion 230 engages clutch head portion 742, rotational or axial force applied to second clutch portion 230, for example by any of Levers A, C and D, such force is transmitted to core rod 710 and to components housed within inner clutch sleeve 610.

Drive clutch 740 has distal annular wall portions 746 arranged to interleave with and abut corresponding circumferentially spaced annular wall portions 840 to limit excessive distal movement of drive clutch 740 responsive to second clutch portion 230 and permit a clutching action for rotation transfer.

Referring now to FIGS. 8A to 8D, an unactuated position of device 100 is described. In the unactuated position, first and second clutch portions 220, 230, anvil 186 and drive clutch 740 are located in relatively proximal positions according to their limited freedom of movement within their respective housings. In this state, because of the position of limiting rod 812 within limiting channel 512, outer clutch sleeve 510 and inner clutch sleeve 610 cannot rotate relative to each other and limiting rod 812 is prevented from rotating relative to outer clutch sleeve 510. As a result, inner delivery sleeve 820 is prevented from rotating within outer delivery sleeve 550.

In the unactuated state, distal end cap 145 is at its proximal-most position, in which open end 148 of domed-shaped apron 147 partially overlies distal delivery tip 142, thereby hindering accidental protrusion of staples 910 from delivery tip 142 prior to their intended release.

It is intended that staples 910 be inserted into staple receiving chambers 826 in their deformed (straightened) configuration when device 100 is in the unactuated state.

Referring now to FIGS. 9A to 9D, device 100 is described in relation to a first actuation state, which is one of several possible actuation states. The first actuation state is achieved by forcing lever 150 to move proximally, for example by squeezing fingers to cause them to curl inwardly towards a hand gripping handle 110, so as to move trigger foot 155 inwardly by one ratchet position. The levering action of trigger 150 about trigger pivot pin 151 causes split claw 154 to move distally. This in turn forces second clutch portion 230 in a distal direction, which in turn causes drive clutch 740 and core rod 710 to move distally by a certain amount, such as a few millimeters, for example.

After the first actuation, distal annular wall portions 746 of drive clutch 740 advance to be adjacent proximal annular wall portions 840, so as to be able to rotationally engage therewith. Thus, distal annular wall portions 746 effectively provide interleaving fingers to interleave with corresponding proximal annular wall portions 840 in order to transmit rotational force from drive clutch 740 to annular wall portions 840, which are in turn rigidly coupled to limiting rod 812 and inner delivery sleeve 820. In the first actuation state, limiting rod 812 remains in its proximal-most position within limiting channel 512. The purpose of the first actuation is to distally progress distal end cap 145 so as to allow subsequent protrusion of staples 910 from distal delivery tip 142 and to engage drive clutch 740 with annular wall portions 840 (to act as a clutch).

Referring now to FIGS. 10A to 10D, a second actuation state of device 100 is described in further detail. In the second actuation state, head retraction actuator 170 (Lever B) is twisted so that, instead of bar 171 being generally horizontal and parallel to barrel housing 410, it is rotated 90 degrees anticlockwise (as seen in FIG. 10A) so that bar 171 is positioned vertically. By thus rotating bar 171, rotation key 173 is caused to rotate counter-clockwise, which causes cam 175 to engage distal face 611a of proximal end flange 611 to shift inner clutch sleeve 610 in a proximal direction by an amount configured according to the shape of clutch 175. For example, inner clutch sleeve 610 may be moved proximally by about 0.5 mm under the action of cam 175.

Retraction in the proximal direction of inner clutch sleeve 610 causes expander rod 650 to be shifted proximally by the same amount, while core rod 710, outer delivery sleeve 550 and inner delivery sleeve 820 remain unmoved, except for a slight flaring of outer delivery sleeve 550 at distal tip 142, as described previously. The flaring of delivery portion 140 is caused by the action of the angled outer surface 662 of expander head 660 acting on the angled inner profile 558 of fingers 552, thereby outwardly deflecting fingers 552. This flaring of distal tip 142 may be configured to result in an increased diameter of approximately 1 to 2 mm, for example.

The second actuation step achievable by actuation of head retraction actuator 170 is not necessary to achieve release of the staples 910, but may be desirable to provide greater expansion of a vessel wall. It is considered that this may provide improved stapling quality.

Referring now to FIGS. 11A to 11D, third and fourth actuation states are described in further detail. In the third actuation state, trigger 150 is depressed proximally in a further step so that trigger foot 155 rests proximally of ratchet projection 113c, which causes split claw 154 to further advance second clutch portion 230 in a distal direction. This causes inner sleeve 820 to be pushed distally by drive clutch 740, thereby advancing staples 910 positioned within staple receiving chambers 826. When staples 910 are received within staple receiving chambers 826, jagged or irregular inner chamber walls 822 partially defining the staple receiving chambers 826 serve to frictionally engage staples 910 so as to encourage them to advance within their respective chambers. An additional or alternative advancement means is provided by inward detent 828 formed in inner delivery sleeve 820 to coincide with staple receiving chambers 826. The inward detents 828 are formed so as to allow each staple 910 to at least partially nest therein based on their shape memory, which is configured to cause them to adopt an approximately circular deployed configuration. As inner delivery sleeve 820 progresses distally, inner chamber walls 822 and/or inward detents 828 assist in moving staples 910 so that one end thereof passes through staple protrusion slots 664 and extends somewhat radially outwardly from tip portion 142. This third actuation state allows for partial protrusion of the staples 910, for example to cause them to protrude at least partially through a graft positioned around delivery tip 142.

Figure 13A:
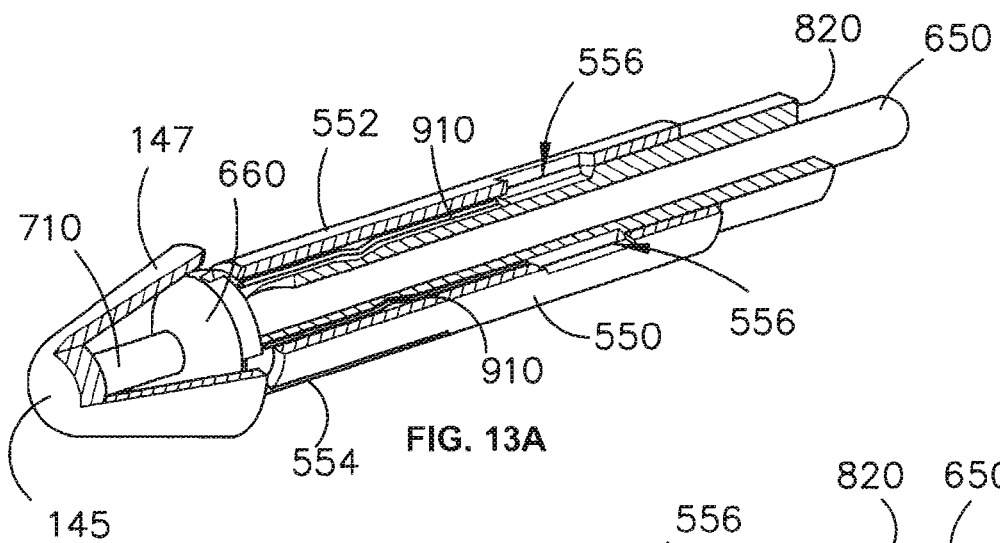
FIG. 13A is a partial cutaway perspective view of a delivery portion of the device of FIG. 1, showing the delivery portion in the unactuated state.
Figure 13B:
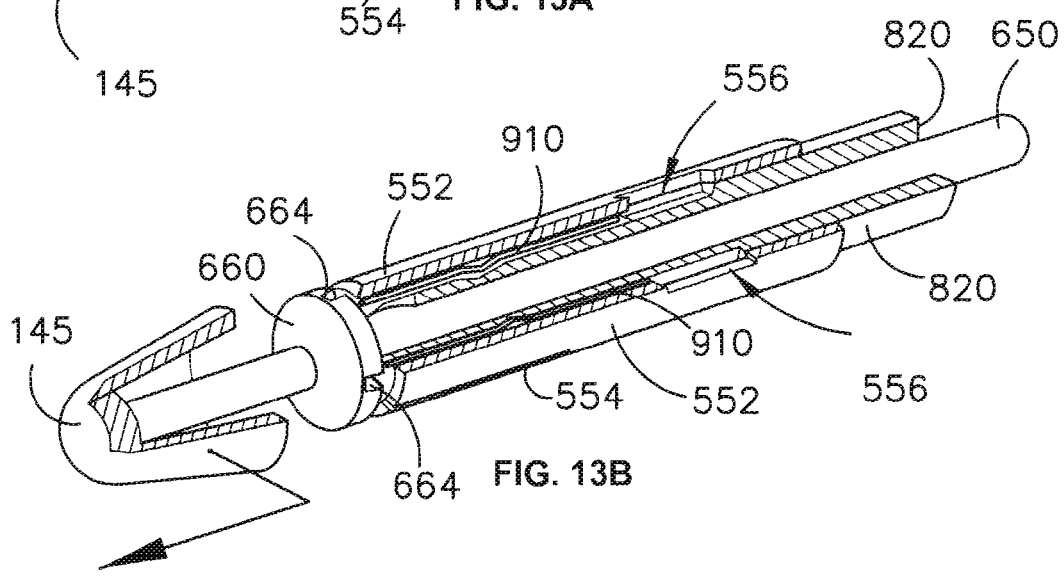
FIG. 13B is a partial cutaway perspective view of the delivery portion, with the device in the partially actuated state.
Figure 13C:
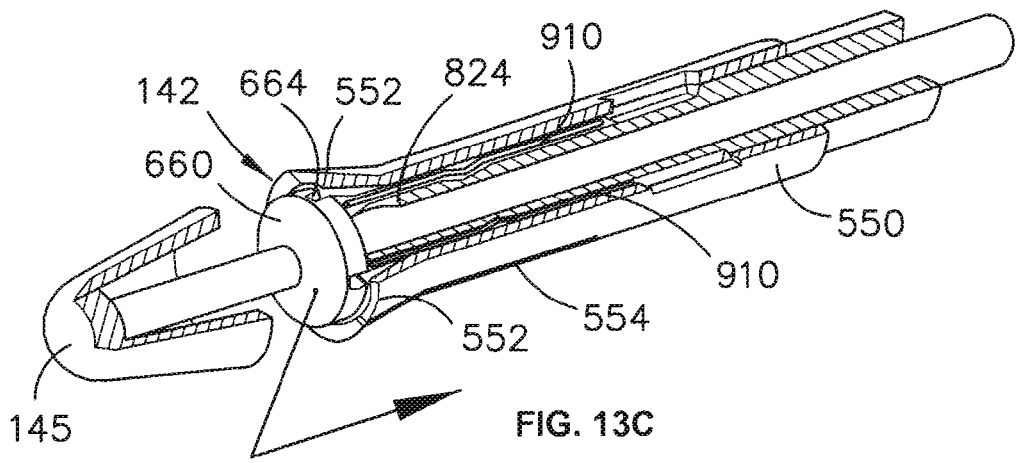
FIG. 13C is a partial cutaway perspective view of the delivery portion, with the device in the further actuated state.
Figure 14A:
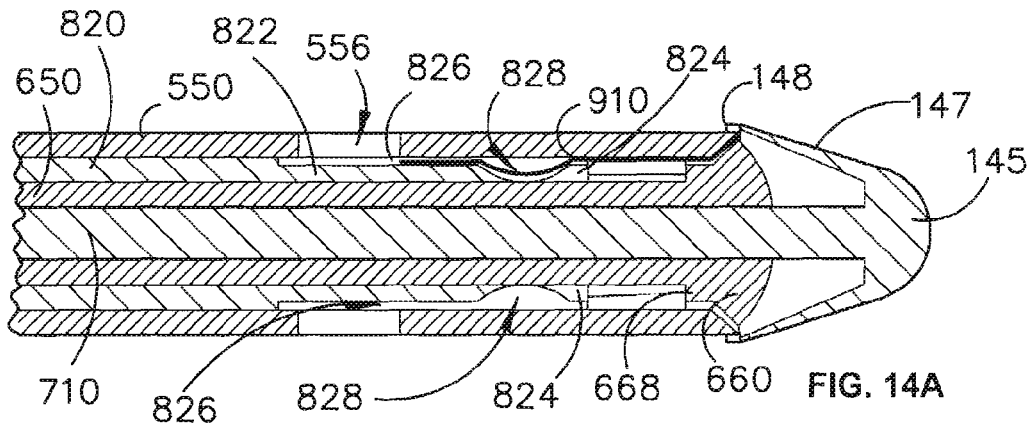
FIG. 14A is a partial side sectional view of the delivery portion, shown when the device is in the unactuated state.
Figure 14B:
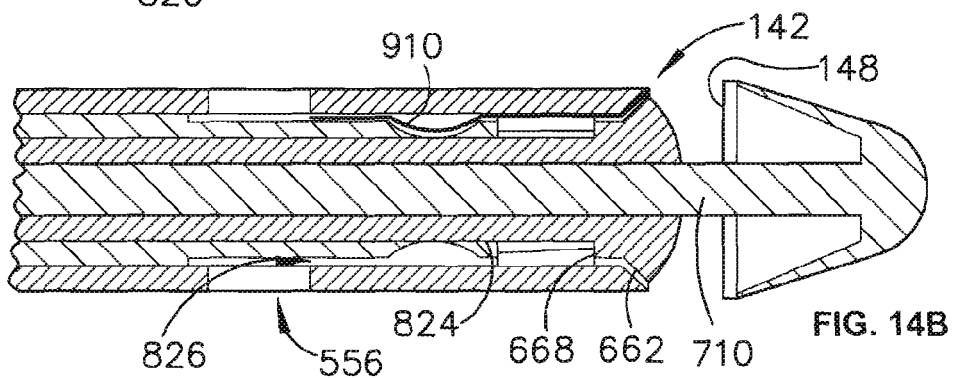
FIG. 14B is a partial side sectional view of the delivery portion, shown with the device in the partially actuated state.
Figure 14C:
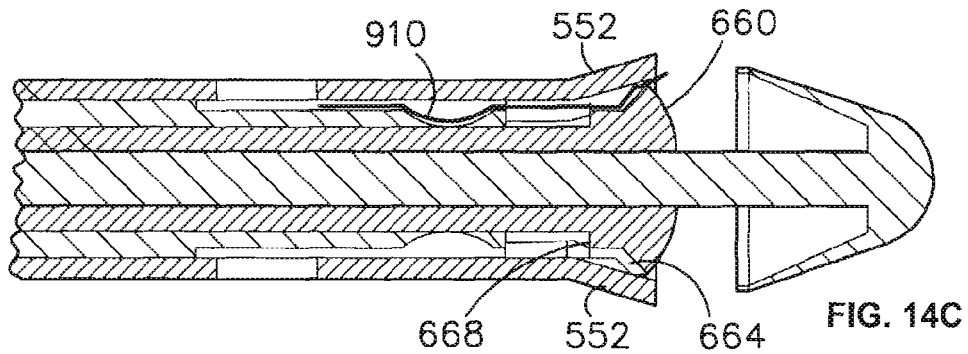
FIG. 14C is a partial side sectional view of the delivery portion, when the device is in the further actuated state.
Figure 14D:
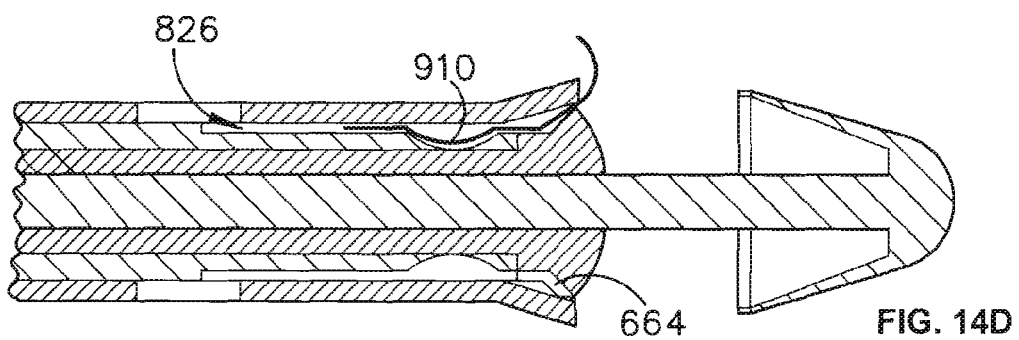
FIG. 14D is a partial side sectional view of the delivery portion, when the device is in the still further actuated state.

Inward detents 828 are formed as radially inwardly curved (concave) deformations in inner delivery sleeve 820 adjacent delivery sleeve distal ends 824. Detents 828 provide axial engagement as well as suitable orientation of the staples 910 so that when freed, the staples 910 have their ends come together at a position outside and away from delivery portion 140 (as illustrated in FIGS. 13E and 14A). If the staples 910 are not oriented properly within receiving chambers 826, their ends may not come together in the right position to achieve the desired stapling effect.

In a fourth actuation state, striking mechanism 190 is actuated to deliver a striking blow to inner delivery sleeve 820 within delivery portion 140. The striking blow is communicated to delivery portion 140 by the application of a moment to lever 180 so as to rotate striking piston 185 and lever 180 into a position where spring 183 biases the striking portion 185 in a distal direction, thereby causing striking piston 185 to act as a hammer upon anvil 186, which communicates the kinetic impact of the hammer blow to second clutch portion 230 via striking transmission portion 188 of anvil 186. Second clutch portion 230 thus receives a kinetic impulse in the distal direction, which is communicated to drive clutch 740 through abutting contact of second clutch portion 230 with drive clutch 740. Drive clutch 740 in turn communicates the kinetic impulse to annular wall 840 which is coupled to the inner delivery sleeve 820.

The distally directed kinetic impulse communicated from the striking mechanism 190 is configured to cause further protrusion of the protruding staples 910 in an approximately stabbing manner. The intention of such stabbing protrusion of staples 910 is to cause protruding ends of staples 910 to be able to break through relatively dense tissue or substances that may have formed on the vessel walls where the join is desired to be made.

Delivery of the striking blow in response to actuation of the striking mechanism 190 is an optional step that can be omitted if desired. Additionally, according to some embodiments, striking mechanism 190 may provide more than one circumferential slot position for lever 180. This is so that greater or lesser compression of spring 183 in the proximal direction may be achieved in order to provide greater or lesser kinetic impact upon anvil 186 when striking mechanism 190 is actuated.

Referring also to FIGS. 12A and 12B, a fifth and final actuation state is described in further detail. Because the advancement of drive clutch 740 also distally advanced annular wall 840 and therefore advanced limiting rod 812 relative to outer clutch sleeve 510, completion of the third actuation state enables the final actuation state (i.e. release of the staples) to be performed. This is because the distal movement of limiting rod 812 relative to outer clutch sleeve 510 and limiting channel 512 positions limiting rod 812 to be able to slide laterally within limiting channel 512. This allows rotation of inner delivery sleeve 820 within outer delivery sleeve 550 as shown in FIGS. 12A and 12B, so that the longitudinally extending staple receiving chambers 826 coincide with release apertures 554, thereby freeing staples 910 to adopt a circular deployed configuration (920) according to their shape memory.

Because of the thinness of the wire used for staples 910, 920 and the strong shape memory induced in such staples, the ends of the staples are sharp enough and come together with enough force to penetrate the tissue surrounding delivery tip 142. Although FIGS. 11A to 11D, 12A and 12D show the distal delivery tip 142 being flared, this need not necessarily be the case. Actuation of staple release actuator 165 causes release of staples 910 through release apertures 554 whether delivery tip 142 is flared or not.

The rotation of inner delivery sleeve 820 relative to outer delivery sleeve 550 is caused by application of a moment to staple release actuator 165, such as by pressing it downwardly. Such a downward movement applied to staple release actuator 165 (Lever D) causes rotation of first clutch portion 220, which transmits rotational movement to annular wall portions 840 via a second clutch portion 230 and drive clutch 740. As annular wall portions 840 are coupled to inner delivery sleeve 820, the downward moment applied to Lever D causes the longitudinally extending staple receiving chambers 826 to align with release apertures 554 to allow staples 910 to spring outwardly and adopt their deployed configuration.

FIGS. 13A, 13B, 13C, 13D and 13E illustrate the unactuated state, the first actuated state, the second actuated state, the third actuated state and the fifth and final actuated state, progressively. Illustration of the further projection resulting from actuation of the striking mechanism 190 is not shown as a'distinct state separate to that of FIG. 13D, but FIG. 13D may be considered to depict the result of a combination of the third and fourth actuation states, as described above.

Figure 14E:
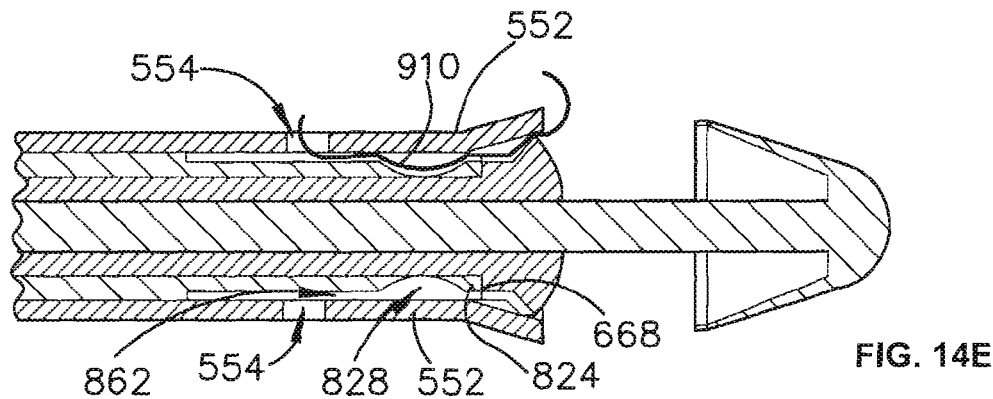
FIGS. 14E, 14F and 14G illustrate a progressive sequence of release of the staples to a deployed configuration, illustrating the delivery portion in partial side cross-section.
Figure 14F:
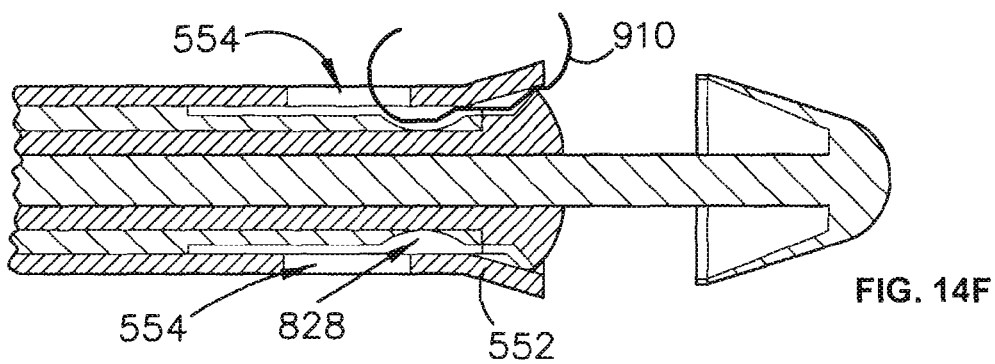
Figure 14G:
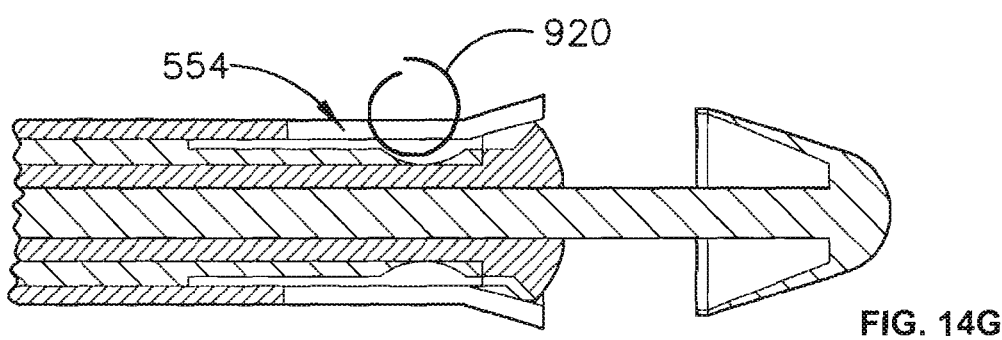
Figure 15:
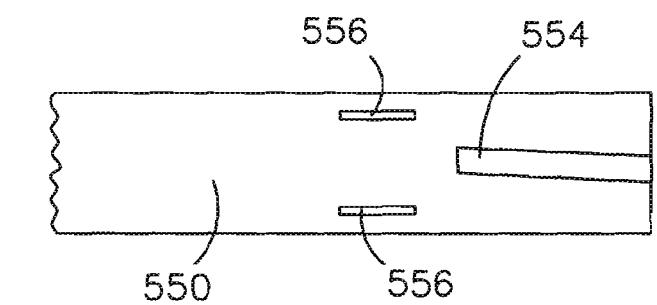
FIG. 15 is a partial plan view of a delivery sleeve of the device, showing insertion apertures and a release aperture for the staples.

Similarly, FIGS. 14A to 14G illustrate the configuration of delivery portion 140 during progressive actuation states. FIGS. 14A, 14B, 14C and 14D respectively correspond to the unactuated state, the first actuation state, the second actuation state and third and fourth actuation states. FIGS. 14E, 14F and 14G progressively illustrate the fifth actuation state, in which the release of staples 910 from release apertures 554 is illustrated for embodiments of device 100 in which release apertures 554 are formed to have a slight spiral (i.e. to be slightly angled relatively to a longitudinal axis, as illustrated in FIG. 15).

For embodiments in which the release apertures 554 are angled, the release apertures 554 are configured so that, while distal ends of the staples 910 protrude from delivery tip 142, at an initial stage of release only a proximal part of release apertures 554 comes into alignment with the underlying staple receiving chambers 826. This allows a proximal end of each staple 910 to begin to curl outwardly from chambers 826 as a result of its shape memory. This initial protrusion of the proximal ends of staples 910 at the beginning of the release stage is illustrated in FIG. 14E.

As can be seen in FIG. 14F, as inner delivery sleeve 820 progressively comes more into alignment with release apertures 554, more of the proximal end of each staple is freed to adopt its deployed configuration, although the staple 910 is not yet completely freed. As FIG. 14F illustrates, the proximal end of each staple 910 tends to curl upwardly so that, once the inner delivery sleeve 820 is brought into further alignment with release apertures 554, as shown in FIG. 14G the opposite ends of each staple 910 are allowed to come together in a pinching and piercing action which is considered to be more effective for some stapling purposes than if there were no progressive release of the proximal end of each staple 910.

Although FIGS. 14A to 14G illustrate the release of only one staple 910 into a deployed configuration 920, this is for simplicity of illustration only and it should be understood that multiple staples are released at the same time from a number of different circumferentially spaced positions. Device 100 can be configured to have four, five, six, seven, eight, nine, ten, eleven or twelve release apertures 554 (and a corresponding number of insertion apertures 556), depending on which configuration may be suited for a particular stapling application. Additionally, although staples 910 appear to be bent between shoulder 668 and delivery tip 142 in FIGS. 14A to 14F, such bending of the staple does not occur in quite the way it is illustrated. Rather, such bending, if it occurs, will be rather smooth, instead of being a sharp bend in the wire.

The angle of release apertures relative to the longitudinal axis of outer delivery sleeve 550 is relatively shallow, such as about 1 degree to about 7 degrees, for example. The angle may be varied, depending on the number of release apertures 554 provided in delivery portion 140.

The wire used as staples 910, 920 may be nitinol wire, for example, with a diameter of between about 0.1 mm to about 0.5 mm. Some specific embodiments are configured to deploy staples of about 0.3 mm or about 0.33 mm in diameter.

The use of shape-memory staples as described herein avoids the need for staples to be deformed by being forced against an anvil to adopt the desired staple shape, thus obviating the extra components and logistical difficulties associated with having an anvil at the staple delivery end of the stapler.

While embodiments are described herein in specific detail, it is to be understood that such embodiments are described by way of example and are not to be construed to be limiting with respect to equivalents or to limit the scope of the invention.

Throughout this specification and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

PARTS LIST 100 stapler
110 handle
111 palmar grip
112 ratchet
112a bolt holes
113a, b, c ratchet projections
114 handle base
114a base bolts
115 movement limiting bolt
116 biasing spring
117 spring registration boss
118 retention bolt
120 actuation portion
122 proximal actuation portion
124 distal actuation portion
128 retention cap
130 shaft
140 delivery portion
142 delivery tip
145 distal end cap
147 apron
148 open end of apron
150 trigger (Lever A)
151 trigger pivot pin
152 finger grip portion
153 pin hole
154 split claw
155 ratchet engagement portion/trigger foot
160 proximal drive mechanism
162 proximal'drive sleeve
164 proximal end insert
165 staple release actuator (Lever D)
166 proximal end screw
170 head retraction actuator (Lever B)
171 bar
172 ball
173 rotation key
174 bar receiving channel
175 cam
176 registration barrel
177 screw thread
178 top screw
180 striking actuator (Lever C)
181 striking actuator housing
182 guide channel
183 striking actuator spring
184 inner cap
185 striking piston/hammer
186 anvil
187 end cap
188 striking transmission portion
190 striking mechanism
211 insert locator pin
212 drive spring
214 radial aperture
216 slotted aperture
218 threaded cylindrical wall
220 first clutch portion
222 clutch proximal end
224 threaded hole
226 keying end
230 second clutch portion
232 first slotted end
234 neck portion
236 second slotted end
250 spring
260 positioning element
312 positioning flange
314 distal end
322 positioning boss
410 barrel housing
412 threaded proximal end
414 actuator insertion port
416 threaded distal end
418 screw receiving aperture
420 internal annular flange
422 registration boss 426 internal thread
432 internal annular flange
440 actuator clutch
442 external annular flange
510 outer clutch sleeve
512 release actuator limiting channel
514 aperture for locating cylinder
516 screw aperture
522 registration notch
524 outer sleeve proximal end opening
526 outer sleeve distal end opening
530 positioning ring
536 fixation screw
537 fixation aperture
536 fixation screw
542 outer sleeve distal end
546 annular wall
550 outer delivery sleeve
552 fingers
554 release aperture
556 insertion apertures
558 angled inner profile
562 spring
610 inner clutch sleeve
611 proximal end flange
611a distal face of proximal end flange
612 release actuator limiting channel
614 aperture for locating cylinder
616 screw aperture
618 inner sleeve distal end
630 locating cylinder
632 diametrical through-hole
636 fixation screw
650 expander rod
651 cylindrical wall
652 proximal end
660 expander head
662 angled outer surface
664 staple protrusion slots
668 shoulder
710 core rod
712 rod proximal end
714 rod distal end
720 locating cylinder
722 diametrical through-hole
730 fixation screw
740 drive clutch
742 clutch head portion
743 central bore
744 transverse bore
746 distal annular wall portions of drive clutch
812 release actuator limiting rod
820 inner delivery sleeve
822 chamber inner wall
824 delivery sleeve distal end
826 staple receiving chambers
828 inward detent
840 annular wall portions (coupled to inner delivery sleeve)
910 staples (deformed configuration)
920 staples (deployed configuration)

The invention claimed is:

1. An apparatus comprising:
a plurality of chambers for receiving an associated plurality of staples, each formed with a shape memory that allows the staple to adopt a straightened configuration, when placed in a stapler, and a deployed configuration for stapling when released from the stapler; and
a sleeve moveable relative to the chambers between a first position, in which the staples are trapped by the sleeve within the chambers in the straightened configuration, and a second position, whereby the staples are freed to adopt the deployed configuration, wherein the sleeve is adapted to move between the first and second positions by rotating relative to the chambers.

2. The apparatus as claimed in claim 1, wherein the shape memory is at least partially thermally activated.

3. The apparatus of claim 1, wherein the sleeve has a plurality of openings which serve as entry points for staples to be loaded into the chambers and wherein the sleeve has a plurality of elongate exit grooves for discharge of the staples into the deployed configuration.

4. The apparatus of claim 3, wherein the exit grooves are radially offset from the openings.

5. The apparatus of claim 3, further comprising a carrier that comprises the chambers and the chambers are arranged to initially align with the openings for loading the staples into the carrier and to subsequently align with the exit grooves when the sleeve is rotated relative to the carrier for discharge of the staples.

6. The apparatus of claim 1, further comprising means for restricting the staples from premature discharge.

7. The apparatus of claim 1, wherein each chamber defines a detent into which the associated staple is free to deform.

8. The apparatus of claim 1, further comprising a lever, a drive mechanism and hand piece with a trigger, wherein the lever allows the drive mechanism to be rotated after the trigger has been initially activated.

9. An apparatus as claimed in claim 1, in the form of a medical stapler.

10. The apparatus as claimed in claim 9 including a cap for holding a graft on an end of the stapler until the staples are deployed.

* * * * *